(12) United States Patent
Harbige et al.

(10) Patent No.: US 7,964,641 B2
(45) Date of Patent: Jun. 21, 2011

(54) TREATMENT OF NEURODEGENERATIVE CONDITIONS

(75) Inventors: Laurence S. Harbige, London (GB); Michael J. Leach, London (GB); Mohammed Sharief, Kent (GB); Paul Barraclough, Surrey (GB)

(73) Assignee: BTG International Limited, London (GB)

( * ) Notice: Subject to any disclaimer, the term of this patent is extended or adjusted under 35 U.S.C. 154(b) by 736 days.

(21) Appl. No.: 10/567,778

(22) PCT Filed: Aug. 13, 2004

(86) PCT No.: PCT/GB2004/003524
§ 371 (c)(1), (2), (4) Date: Feb. 9, 2007

(87) PCT Pub. No.: WO2005/018632
PCT Pub. Date: Mar. 3, 2005

(65) Prior Publication Data
US 2008/0194684 A1 Aug. 14, 2008

(30) Foreign Application Priority Data

Aug. 18, 2003 (GB) .................................. 0319358.8
May 14, 2004 (GB) .................................. 0410846.0

(51) Int. Cl.
*A61K 31/201* (2006.01)
*C07C 57/03* (2006.01)
*A61P 25/00* (2006.01)

(52) U.S. Cl. ...................................... 514/560; 554/224

(58) Field of Classification Search ........................ None
See application file for complete search history.

(56) References Cited

U.S. PATENT DOCUMENTS

| 2,077,371 A | 4/1937 | Relneck et al. |
| 2,617,791 A | 11/1952 | Snelling et al. |
| 3,082,228 A | 3/1963 | Sutherland et al. |
| 3,158,541 A | 11/1964 | Sutherland et al. |
| 3,558,656 A | 1/1971 | Pfieffer et al. |
| 3,658,555 A | 4/1972 | Menz et al. |
| 3,671,557 A | 6/1972 | Pfieffer et al. |
| 3,671,563 A | 6/1972 | Pfieffer et al. |
| 3,676,472 A | 7/1972 | Zilliken et al. |
| 3,748,348 A | 7/1973 | Sreenivasan et al. |

(Continued)

FOREIGN PATENT DOCUMENTS

EP 0 505 817 A 9/1992

(Continued)

OTHER PUBLICATIONS

The Merk Manual, Fifteenth Edition, 1987, pp. 1421-1424.*

(Continued)

*Primary Examiner* — Ardin Marschel
*Assistant Examiner* — Bong-Sook Baek
(74) *Attorney, Agent, or Firm* — Nixon & Vanderhye

(57) ABSTRACT

A method is provided for treating a patient in need of therapy for a neurodegenerative disease comprising administering to that patient a therapeutically effective dose of a lipid glyceride comprising a glycerol moiety and a fatty acid moiety, the fatty acid moiety being selected from the group consisting of γ-linolenic acid, dihomo-γ-linolenic acid and arachidonic acid characterized in that the selected fatty acid moiety is attached to the glycerol moiety at its sn-2 position. Preferably the method is that wherein the lipid is administered for a duration and at a dose sufficient to maintain or elevate TGF-β1 levels in the patient to therapeutic levels.

4 Claims, 17 Drawing Sheets

U.S. PATENT DOCUMENTS

Figure 1:
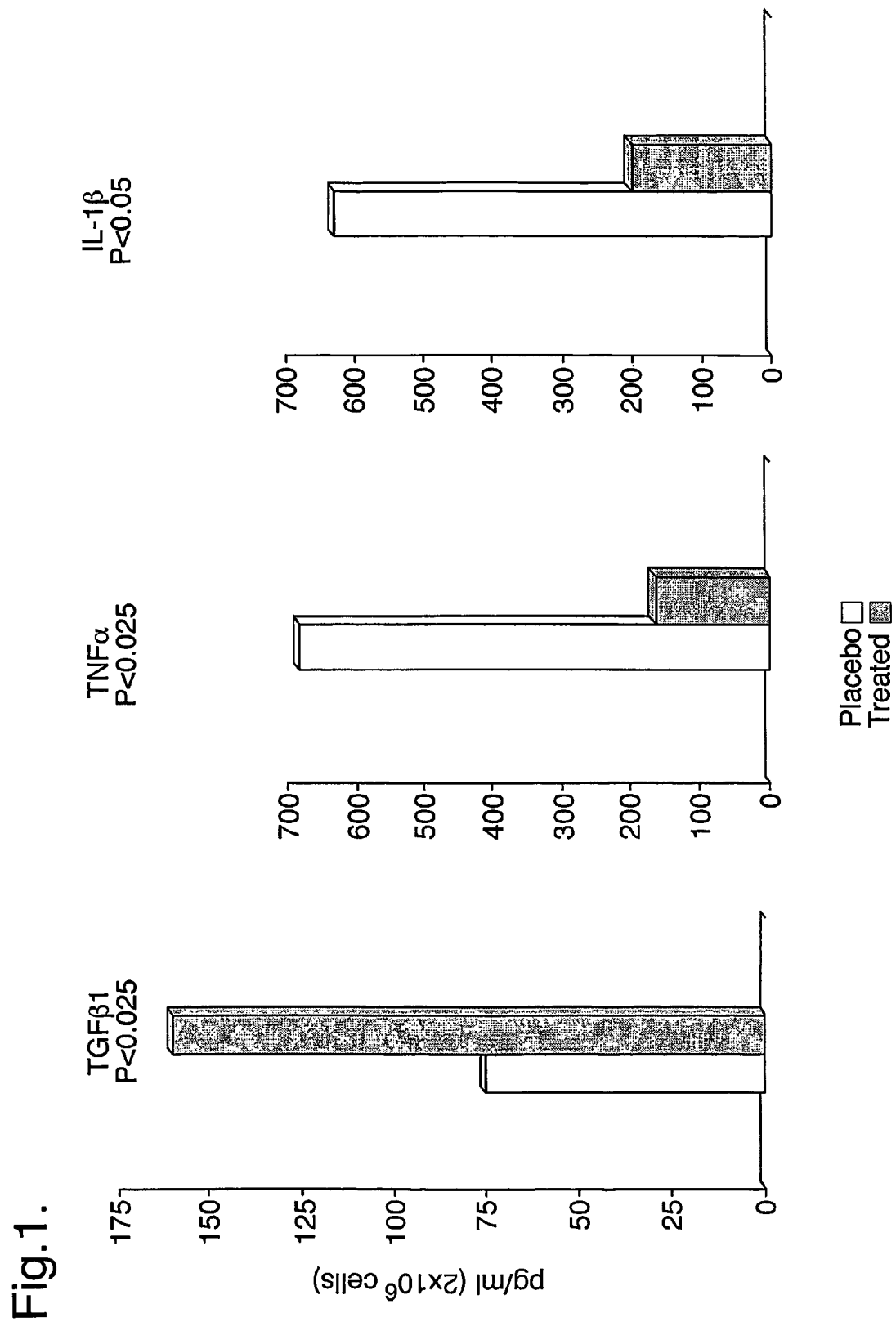

| | | | |
|---|---|---|---|
| 3,855,254 A | 12/1974 | Haighton et al. | |
| 3,862,972 A | 1/1975 | Heslinga et al. | |
| 3,972,907 A | 8/1976 | Baran et al. | |
| 3,993,775 A | 11/1976 | Williams | |
| 4,048,202 A | 9/1977 | Beek et al. | |
| 4,058,594 A | 11/1977 | Williams | |
| 4,181,670 A | 1/1980 | Liang et al. | |
| 4,607,052 A | 8/1986 | Mendy et al. | |
| 4,622,180 A | 11/1986 | Paltauf et al. | |
| 4,701,468 A | 10/1987 | Mendy et al. | |
| 4,701,469 A | 10/1987 | Mendy et al. | |
| 4,826,877 A | 5/1989 | Stewart et al. | |
| 4,832,975 A | 5/1989 | Yang | |
| 4,851,343 A | 7/1989 | Herbert et al. | |
| 4,867,965 A | 9/1989 | Ciaudelli | |
| 4,876,107 A | 10/1989 | King et al. | |
| 4,938,984 A | 7/1990 | Traitler et al. | |
| 5,008,126 A | 4/1991 | Klenmann et al. | |
| 5,077,312 A | 12/1991 | Shoyab et al. | |
| 5,151,291 A | 9/1992 | Tokairin et al. | |
| 5,227,403 A | 7/1993 | Seto et al. | |
| 5,306,730 A | 4/1994 | Nagai et al. | |
| 5,583,159 A | 12/1996 | Horrobin et al. | |
| 5,618,955 A | 4/1997 | Mechoulam et al. | |
| 5,658,767 A | 8/1997 | Kyle et al. | |
| 5,661,180 A | 8/1997 | DeMichele et al. | |
| 5,663,202 A | 9/1997 | Horrobin et al. | |
| 5,668,174 A | 9/1997 | Kawagishi et al. | |
| 5,674,901 A | 10/1997 | Cook et al. | |
| 5,753,702 A | 5/1998 | Bednar et al. | |
| 5,776,913 A | 7/1998 | Olgilvie et al. | |
| 5,834,512 A | 11/1998 | Akimoto et al. | |
| 5,837,731 A | 11/1998 | Vaddadi | |
| 5,869,537 A | 2/1999 | Schreiner et al. | |
| 5,914,347 A | 6/1999 | Grinda | |
| 5,922,345 A | 7/1999 | Horrobin et al. | |
| 5,962,712 A | 10/1999 | DeMichele et al. | |
| 5,968,809 A | 10/1999 | Knutzon et al. | |
| 5,981,588 A | 11/1999 | Akimoto et al. | |
| 5,990,163 A | 11/1999 | Evans et al. | |
| 6,015,798 A | 1/2000 | Ogilvie et al. | |
| 6,020,376 A | 2/2000 | Pariza et al. | |
| 6,051,754 A | 4/2000 | Knutzon et al. | |
| 6,080,787 A | 6/2000 | Carlson et al. | |
| 6,184,251 B1 | 2/2001 | Stordy et al. | |
| 6,201,022 B1 | 3/2001 | Mease et al. | |
| 6,214,372 B1 | 4/2001 | Jerome et al. | |
| 6,262,119 B1 | 7/2001 | Ferrante et al. | |
| 6,306,908 B1 | 10/2001 | Carlson et al. | |
| 6,331,568 B1 | 12/2001 | Horrobin et al. | |
| 6,340,485 B1 | 1/2002 | Coupland et al. | |
| 6,340,705 B1 | 1/2002 | Obukowicz et al. | |
| 6,361,806 B1 | 3/2002 | Allen et al. | |
| 6,369,252 B1 | 4/2002 | Akoh | |
| 6,410,078 B1 | 6/2002 | Cain et al. | |
| 6,410,288 B1 | 6/2002 | Knutzon et al. | |
| 6,426,100 B2 | 7/2002 | Watkins et al. | |
| 6,426,367 B1 | 7/2002 | Das | |
| 6,479,070 B1 | 11/2002 | Cain et al. | |
| 6,479,544 B1 | 11/2002 | Horrobin | |
| 6,495,536 B1 | 12/2002 | Masui et al. | |
| 6,528,040 B1 | 3/2003 | Pearson et al. | |
| 6,537,750 B1 | 3/2003 | Shorrosh | |
| 6,555,579 B2 | 4/2003 | Kritchevsky | |
| 6,566,543 B2 | 5/2003 | Mechoulam et al. | |
| 6,576,252 B2 | 6/2003 | Schwartz et al. | |
| 6,624,195 B2 | 9/2003 | Horrobin | |
| 6,630,157 B1 | 10/2003 | Horrobin et al. | |
| 6,673,840 B1 | 1/2004 | Oh et al. | |
| 6,677,470 B2 | 1/2004 | Saebo et al. | |
| 6,689,812 B2 | 2/2004 | Peet et al. | |
| 6,841,573 B2 | 1/2005 | Llewellyn | |
| 6,852,757 B2 | 2/2005 | Jerome et al. | |
| 6,858,416 B2 | 2/2005 | Mukerji et al. | |
| 6,864,242 B2 | 3/2005 | Ernest | |
| 2001/0047036 A1 | 11/2001 | Vanderhoof et al. | |
| 2002/0022658 A1 | 2/2002 | Das | |
| 2002/0051964 A1 | 5/2002 | Surai et al. | |
| 2002/0065319 A1 | 5/2002 | Horrobin | |
| 2002/0072539 A1 | 6/2002 | Mechoulam et al. | |
| 2002/0081366 A1 | 6/2002 | Cain et al. | |
| 2002/0082436 A1 | 6/2002 | Jerome et al. | |
| 2002/0198177 A1 | 12/2002 | Horrobin | |
| 2003/0013759 A1 | 1/2003 | Das | |
| 2003/0031753 A1 | 2/2003 | Watkins et al. | |
| 2003/0032674 A1* | 2/2003 | Hwang | 514/560 |
| 2003/0045460 A1 | 3/2003 | Fogelman et al. | |
| 2003/0045578 A1 | 3/2003 | Horrobin | |
| 2003/0166723 A1 | 9/2003 | Nakajima et al. | |
| 2004/0014810 A1 | 1/2004 | Horrobin et al. | |
| 2004/0019109 A1 | 1/2004 | Owman et al. | |
| 2004/0039058 A1 | 2/2004 | Ursin et al. | |
| 2004/0043963 A1 | 3/2004 | Wadstein | |
| 2004/0048926 A1 | 3/2004 | Hoffman et al. | |
| 2004/0048927 A1 | 3/2004 | Horrobin | |
| 2004/0096468 A1 | 5/2004 | Changaris | |
| 2004/0102519 A1 | 5/2004 | Llewellyn | |
| 2004/0162348 A1 | 8/2004 | Peet et al. | |
| 2004/0171688 A1 | 9/2004 | Bar-Tana | |
| 2004/0208939 A1 | 10/2004 | Sears et al. | |
| 2004/0209953 A1 | 10/2004 | Lee | |
| 2004/0220081 A1 | 11/2004 | Kreitz et al. | |
| 2004/0229950 A1 | 11/2004 | Vanderhoek | |
| 2004/0248763 A1 | 12/2004 | Freeman et al. | |
| 2004/0266874 A1 | 12/2004 | Akimoto et al. | |
| 2005/0009779 A1 | 1/2005 | Killiaan et al. | |
| 2005/0025744 A1* | 2/2005 | Lane | 424/85.6 |
| 2005/0027004 A1 | 2/2005 | Kyle et al. | |
| 2005/0042256 A1 | 2/2005 | Decombaz et al. | |
| 2005/0123479 A1 | 6/2005 | Ferrante | |
| 2009/0137660 A1* | 5/2009 | Harbige et al. | 514/452 |

FOREIGN PATENT DOCUMENTS

| | | |
|---|---|---|
| EP | 0 609 078 A | 8/1994 |
| EP | 0490 561 | 3/1996 |
| EP | 0 707 850 | 4/1996 |
| EP | 0 711 503 | 5/1996 |
| EP | 0 766 961 | 4/1997 |
| EP | 0 790 056 | 8/1997 |
| EP | 0 679 057 | 8/1999 |
| EP | 0 568 608 | 9/2000 |
| EP | 0 956 011 | 6/2002 |
| EP | 0 920 300 | 4/2003 |
| EP | 0 956 013 | 4/2003 |
| EP | 0 800 584 | 5/2003 |
| EP | 1 325 747 A2 | 7/2003 |
| EP | 1 325 747 A3 | 7/2003 |
| EP | 1 342 787 | 9/2003 |
| EP | 1 129 711 | 1/2004 |
| EP | 0 994 705 | 3/2004 |
| EP | 1 292 288 | 9/2004 |
| EP | 1 221 867 | 11/2004 |
| EP | 1506778 | 2/2005 |
| GB | 1 490 603 | 11/1977 |
| GB | 2 409 644 | 7/2005 |
| WO | WO 90/12080 | 10/1990 |
| WO | WO 96/05164 | 2/1996 |
| WO | WO 96/40106 | 12/1996 |
| WO | WO 97/04127 | 2/1997 |
| WO | WO 98/16215 | 4/1998 |
| WO | WO 98/44917 | 10/1998 |
| WO | WO 98/46763 | 10/1998 |
| WO | WO 98/46764 | 10/1998 |
| WO | WO 98/46765 | 10/1998 |
| WO | WO 99/51560 A1 | 10/1999 |
| WO | WO 00/09476 | 2/2000 |
| WO | WO 00/12720 | 3/2000 |
| WO | WO 00/21524 | 4/2000 |
| WO | WO 00/34791 | 6/2000 |
| WO | WO 00/40705 | 7/2000 |
| WO | WO 00/44360 | 8/2000 |
| WO | WO 00/53637 | 9/2000 |
| WO | WO 00/74669 | 12/2000 |
| WO | WO 01/10989 | 2/2001 |
| WO | WO 01/13733 | 3/2001 |
| WO | WO 01/17366 | 3/2001 |
| WO | WO 01/17524 | 3/2001 |

| WO | WO 01/97793 A | 12/2001 |
| WO | WO 01/97793 A2 | 12/2001 |
| WO | WO 02/05849 | 1/2002 |
| WO | WO 02/47493 | 6/2002 |
| WO | WO 02/092073 | 11/2002 |
| WO | WO 02/096408 | 12/2002 |
| WO | WO 02/102757 | 12/2002 |
| WO | WO 03/013276 | 2/2003 |
| WO | WO 03/013497 A | 2/2003 |
| WO | WO 03/043972 | 5/2003 |
| WO | WO 03/075003 | 9/2003 |
| WO | WO 03/075670 | 9/2003 |
| WO | WO 03/092628 | 11/2003 |
| WO | WO 2004/012753 | 2/2004 |
| WO | WO 2004/024136 | 3/2004 |
| WO | WO 2004/028529 | 4/2004 |
| WO | WO 2004/084882 | 10/2004 |
| WO | WO 2004/105517 | 12/2004 |
| WO | WO 2005/018632 A1 | 3/2005 |
| WO | WO 2005/037848 | 4/2005 |
| WO | WO 2005/063231 | 7/2005 |

OTHER PUBLICATIONS

Merk Manual regarding Alzheimer's Disease.*
Yuksel et al. Etiologic classification of 4659 patients with mental retardation or multiple congenital abnormality and mental retardation. J. Pediatr. Neurosci. pp. 45-52, 2007.*
Akoh, C.C.; "Structured lipids—enzymatic approach"; *Inform*; vol. 6:9, pp. 1055-1061 (1995).
Bradley, D.G., "Designer fats; turning scientific advance into consumer benefit"; *Lipid Technology*; pp. 89-91, Jul. 1997.
Christensen, M.S., et al; "Intestinal absorption and lymphatic transport of eicosapentaenoic 9EPA), docosahexaenoic 9DHA), and decanoic acids: dependence on intramolecular triacylglycerol structure"; *Am. J. Clin. Nutr.* vol. 61, pp. 56-61 (1995).
Christensen, M.S., et al; "Absorption of triglycerides with defined or random structure by rats with biliary and pancreatic diversion"; *Lipids*; vol. 30, No. 6, pp. 521-526 (1995).
Decker, E.A.; "The role of stereospecific saturated fatty acid positions on lipid nutrition"; *Nutr. Rev.*; vol. 54, No. 4, pp. 108-110 (1996).
Dehesh, K., "Production of high levels of 8:0 and 10:0 fatty acids in transgenic canola by overexpression of Ch FatB2, a thioesterase cDNA from *Cuphea hookeriana*"; *The Plant Journal*; vol. 9, No. 2; pp. 167-172 (1996).
Gurr, M.; "Fat digestion and assimilation"; *Lipid Technology*; pp. 94-97, Jul. 1997.
Hauumann, B.F.; "Structured lipids allow fat"; *Inform* vol. 8, No. 10, pp. 1004-1011 (1997).
Ikeda I., et al; "Lymphatic absorption of structured glycerolipds containing medium-chain fatty acids and linoleic acid, and their effect on cholesterol absorption in rats"; *Lipids*, vol. 26, No. 5, pp. 369-373 (1991).
Jandacek, R.J., et al; "The rapid hydrolysis and efficient absorption of triglycerides with octanoic acid in the 1 and 3 positions and long-chain fatty acid in the 2 position"; *Am J. Clin. Nutr.*; vol. 45, pp. 940-945 (1987).
Jensen, M.M., et al; "Intestinal absorption of octanoic, decanoic, and linoleic acids: Effect of triglyceride structure"; *Ann. Nutr. Metab*, vol. 38, pp. 104-116 (1994).
Kenler A.S., et al; "Early enteral feeding in postsurgical cancer patients"; *Annals of Surgery*; vol. 223, No. 3, pp. 316-333 1996).
Kennedy, J.P.; "Structured Lipids: Fats of the Future"; *Food Technology*; pp. 76-83 (1991).
Kritchevsky, D. ; "Fatty acids, triglyceride structure, and lipid metabolism"; *Nutr. Biochem*, vol. 6, pp. 172-178 (1995).
Kritchevsky, D., et al; "Cholesterol vehicle in experimental atherosclerosis Part 10. Influence of specific saturated fatty acids"; *Exp. Molec. Pathol*; vol. 6, pp. 394-401 (1967).
Kritchevsky, D.; "Cholesterol vehicle in experimental atherosclerosis VII. Influence of naturally occurring saturated fats"; *Med. Pharmacol. Exp.*; vol. 12, pp. 315-320 (1965).
Kritchevsky, D. et al; "Cholesterol vehicle in experimental atherosclerosis Part 15. Randomized butter and randomized lard"; *Atherosclerosis*; vol. 27, pp. 339-345 (1977).
Kritchevsky D., et al; "Experimental atherosclerosis in rabbits fed cholesterol free diets. Part 10. Cocoa butter and palm oil"; Atherosclerosis; vol. 41, pp. 279-284 (1982).
Kritchevsky, D. et al; "Influence of triglyceride structure on experimental atherosclerosis in rabbits"; *FASEB J* 10, A187 (1996).
Kritchevsky D, Tepper SA, Kim HK, Story JA, Vesselinovitch D, and Wissler RW. 1976. Experimental atherosclerosis in rabbits fed cholesterol free diets 5. Comparison of peanut, corn, butter and cocon ut oils. Exp. Molec. Pathol. 24: 375-391.
Kritchevsky, D., et al; "Influence of triglyceride structure on experimental atherosclerosis in rabbits"; *FASEB J* 9, A320 (1995).
Kritchevsky,k D., et al; "Thyroid hormone and experimental atherosclerosis in rabbits"; *Atherosclerosis*; vol. 23, pp. 249-252 (1976).
Kubow, S., et al; "The influence of positional distribution of fatty acids in native, interesterified and structure-specific lipds on lipoprotein metabolism and atherogenesis"; *Nutr. Biochem*; vol. 7, pp. 530-541 (1996).
Mattson, F.H., et al; "The digestion and absorption of triglycerides"; *J. Biol. Chem.*; vol. 239, pp. 2772-2777 (1964).
Metolli, A.M., et al; "Medium-chain lipds: new sources, uses"; *Inform*; vol. 8, No. 6, pp. 597-603 (1997).
Myher, J.J., et al; "Acylglycerol Structure of peanut oils of different atherogenic potential"; *Lipids*; vol. 12; pp. 765-878 (1977).
Sadou, H. et al; "Differential incorporation of fish-oil eicosapentaenoate and docosahexaenoate into lipds of lipoprotein fractions as related to their glycerol esterification: a short-term (postprandial) and long-term study in healthy humans"; *Am J. Clin Nutr.*; vol. 62, pp. 1193-1200 (1995).
Small, D.M.; "The effects of glyceride structure on absorption and metabolism"; *Annu. Rev. Nutr.*; vol. 11, pp. 413-434 (1991).
Voelker, T.A., et al; "Fatty acid biosynthesis redirected to medium chains in transgenic oilseed plants"; *Science*; vol. 257, pp. 72-74 (1992).
Zock, P.L., et al; "Positional distribution of fatty acids in dietary triglycerides: effects on fasting blood lipoprotein concentrations in humans"; *Am. J. Clin. Nutr.*; vol. 61, pp. 48-55 (1995).
Kritchevsky, D.; "Fatty acids, triglyceride structure, and lipid metabolism"; *Nutr. Biochem*; vol. 6, pp. 172-178 (1995).
Miles, E.A., et al; "The influence of different combinations of γ-linolenic acid, stearidonic acid and EPA on immune function in healthy young male subjects"; *British Journal of Nutrition*; vol. 91, pp. 893-903 (2004).
McCormick, J.N., et al; "Immunosuppressive effect of linolenic acid"; *The Lancet*; p. 508 (1977).
Demmelmair, H., et al; "Influence of formulas with borage oil or borage oil plus fish oil on the arachidonic acid status in premature infants"; *Lipids*, vol. 36, No. 6; pp. 555-566 (2001).
Thijs, C., et al; "Essential fatty acids in breast milk of atopic mothers: comparison with non-atopic mothers, and effect of borage oil supplementation"; *European Journal of Clinical Nutrition*; vol. 54, pp. 234-238 (2000).
Leventhal, L.J., et al; "Treatment of Rheumatoid Arthritis with Blackcurrant Seed Oil"; *British Journal of Rheumatology*; vol. 33, pp. 847-852 (1994).
Zurier, R.B., et al; "Gamma-Linolenic Acid Treatment of Rheumatoid Arthritis"; *Arthritis & Rheumatism*; vol. 39, No. 11, pp. 1808-1817 (1996).
Leventhal, L.J., et al; "Treatment of Rheumatoid Arthritis with Gammalinolenic Acid"; *Annals of Internal Medicine*; vol. 119; No. 9; pp. 867-873 (1993).
Co-pending U.S. Appl. No. 10/555,757, filed Nov. 7, 2005.
Co-pending U.S. Appl. No. 11/791,606, filed May 25, 2007.
Co-pending U.S. Appl. No. 11/885,255, filed Aug. 29, 2007.
Lawson, L.D., et al; "Triacylglycerol Structure of Plant and Fungal Oil Containing γ-Linolenic Acid"; *Lipids*, vol. 23, No. 4, pp. 313-317 (1988).
Harbige, L.S., et al; "Prevention of experimental autoimmune encephalomyelitis in Lewis rats by a novel fungal source of γ-linolenic acid"; *British Journal of Nutrition*, vol. 74, No. 5, pp. 701-715 (1995).

Hoy, Carl-Erik, et al; "Absorption of γ-Linolenic Acid from Borage, Evening Primrose, and Black Currant Seed Oils: Fatty Acid Profiles, Triacylglycerol Structures, and Clearance Rates of Chylomicrons in the Rat"; *γ-Linolenic Acid: Metabolism and Its Roles in Nutrition and Medicine*; AOCS Press, Champaign, IL, pp. 54-65, (1996) XP009035802.

Patent Abstracts of Japan, vol. 1995, No. 01, Feb. 28, 1995 & JP 06 279311 A (Sagami Chem Res Center; others: 01), 04 Oct. 4, 1994 (Abstract).

Patent Abstracts of Japan, vol. 1996, No. 03, Mar. 29, 1996 & JP 07 309773 A (Sagami Chem Res Center; others: 01), Nov. 28, 1995 (Abstract).

Mechoulam, R., et al; "Cannabinoids and brain injury: therapeutic implications"; *Trends in Molecular Medicine*; vol. 8, No. 2; pp. 58-61 (2002) XP-002381881.

Database Biosis (Online), Biosciences Information Service, Philadelphia, PA, USA; Mar. 2003; Rockwell C.E., et al; "Inhibition of interleukin-2 (IL-2) by the endogenous cannabinoid, 2-arachidonyl glycerol, is partly mediated through peroxisome proliferators-activated receptor-gamma (PPAR-gamma)"; Database accession No. PREV200300230725 abstract & *Toxicological Sciences*, vol. 72, No. s-1, Mar. 2003, p. 328, 42nd Annual Meeting of the Society of Toxicology; Salt Lake City, UT, USA; Mar. 9-13, 2003, ISSN: 1096-6080.

Database Embase (Online) Elsevier Science Publishers, Amsterdam, N1; 2005, Kaplan, B. L.F., et al; "2-Arachidonoylglycerol suppresses interferon-γ production in phorbol ester/ionomycin-activated mouse splenocytes independent of CB1 or CB2", XP-002381886 (abstract); *Journal of Leukocyte Biology*; vol. 77 pp. 966-974 (2005).

Ouyang, Y., et al; "Suppression of Interleukin-2 by the Putative Endogenous Cannabinoid 2-Arachidonyl-Glycerol is Mediated through Down-regulation of the Nuclear Factor of Activated T Cells"; *Molecular Pharmacology*; vol. 53, pp. 676-683 (1998) XP-002381882.

Venderova, K., et al; "Differential effects of endocannabinoids on [$^3$H]-GABA uptake in the rat *Globus pallidus*"; *Experimental Neurology*; vol. 194, pp. 294-287 (2005).

Yaqoob, P., et al; "Encapsulated fish oil enriched in α-tocopherol alters plasma phospholipid and mononuclear cell fatty acid compositions but not mononuclear cell functions"; *European Journal of Clinical Investigation*; vol. 30; pp. 260-274 (2000).

Levin, G., et al; "Differential metabolism of dihomo-γ-linolenic acid and arachidonic acid by cyclo-oxygenase-1 and cyclo-oxygenase-2: implications for cellular synthesis of prostaglandin $E_1$ and prostaglandin $E_2$"; *Biochem J.*; vol. 365; pp. 489-496 (2002).

Fisher, B.A.C., et al; "Effect of omega-6 lipid-rich borage oil feeding on immune function in healthy volunteers"; *Biochemical Society Transactions*; vol. 25, 343S (1 pg), (1997).

\* cited by examiner

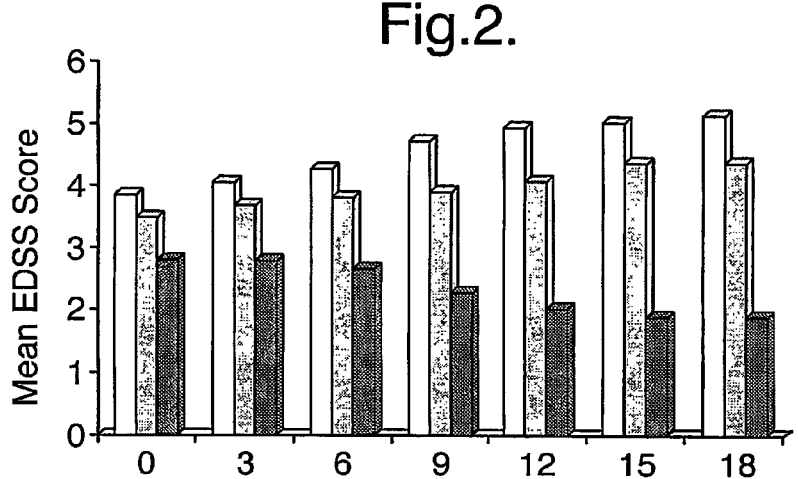
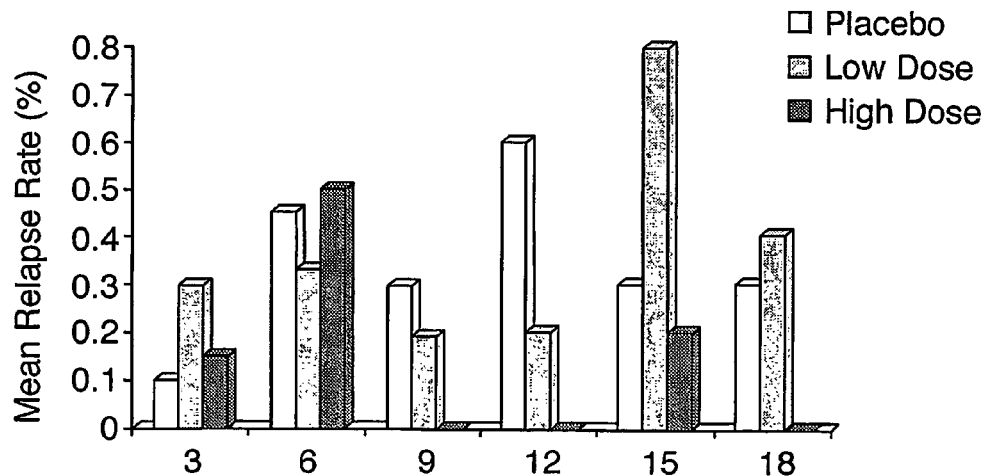

2

Glycerol tris-(6-Z,9-Z,12-Z-octadecatrienoate)   $C_{57}H_{92}O_6$

Tri-gamma-linolenin     MW = 873.4

Numbering systems: black for biologists; blue for chemists

Fig.5.
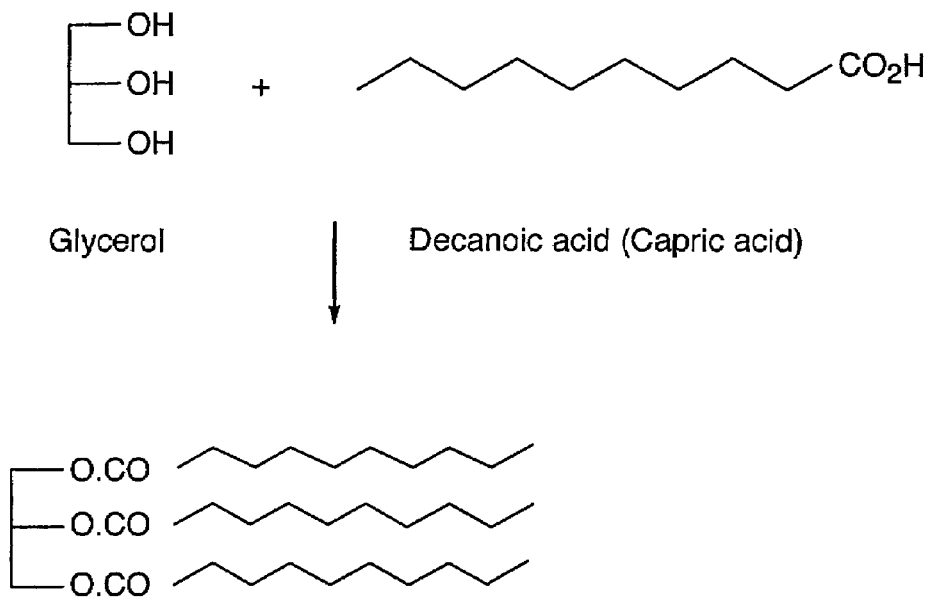
Glycerol        Decanoic acid (Capric acid)
4
Glycerol tridecanoate    $C_{33}H_{62}O_6$
MW=554.85    mp 32°C    Exhibits polymorphism
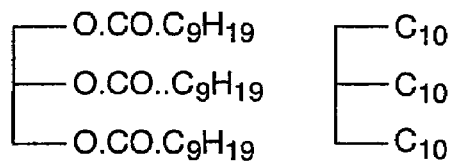

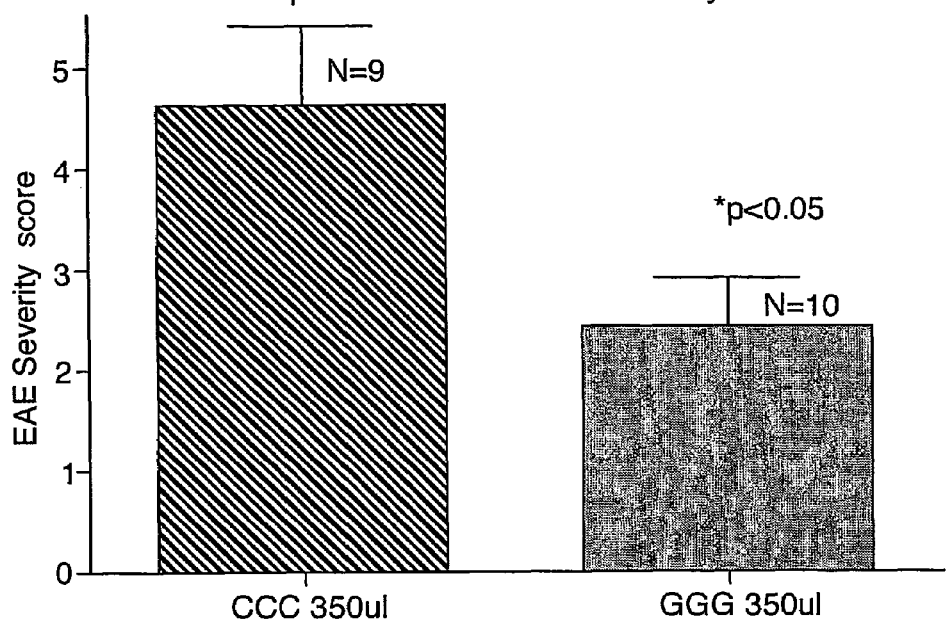
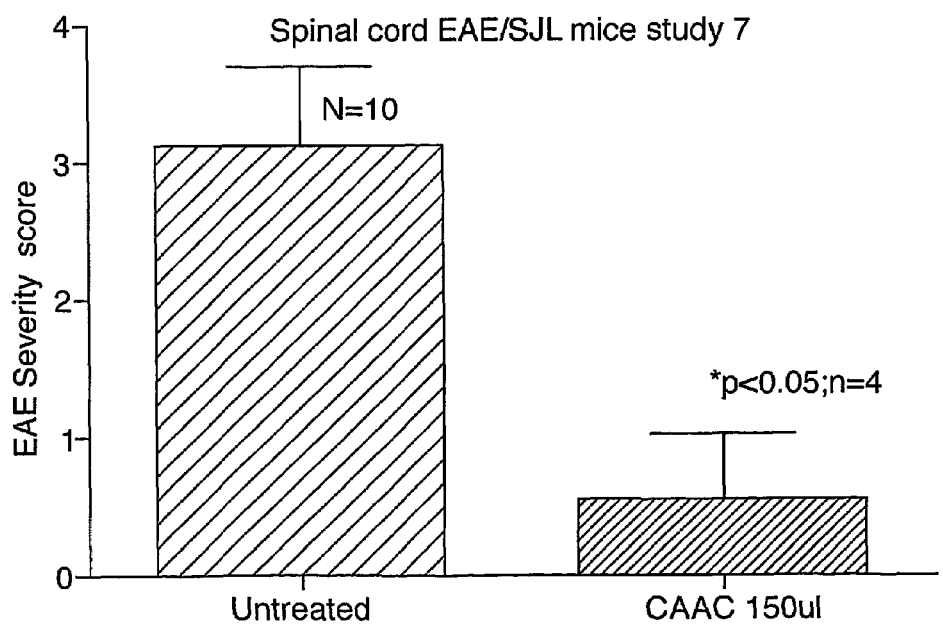
Fig. 10.

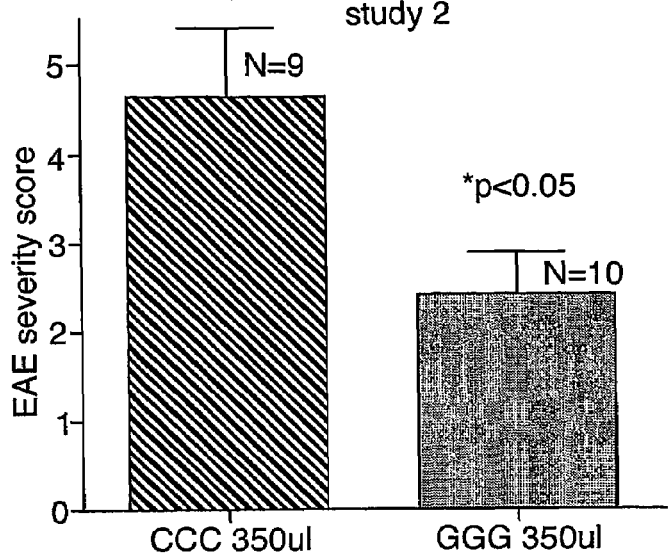
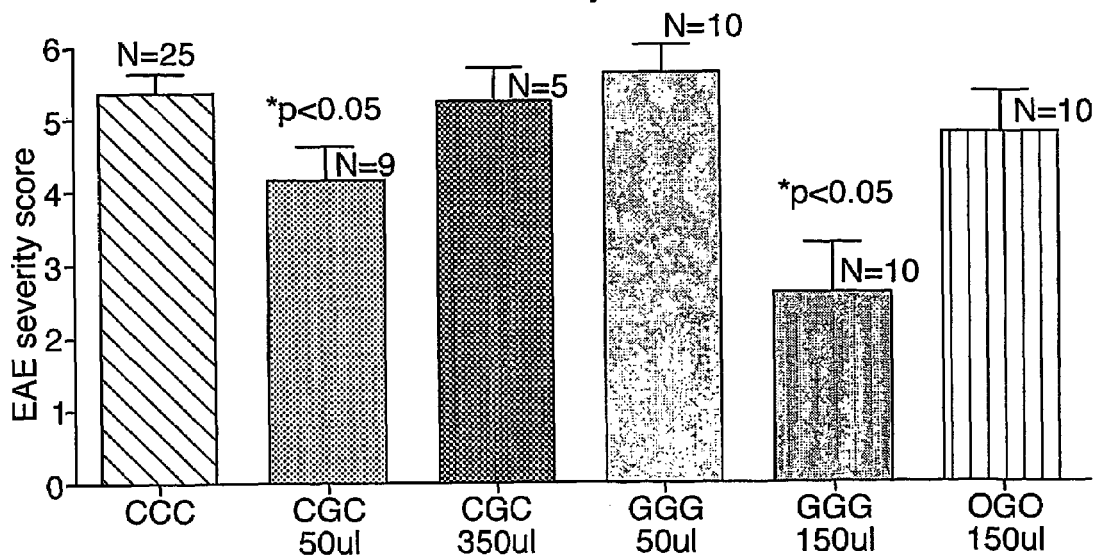
Fig. 11.

Fig. 17.
Study 6: MOG EAE/C57BL mice
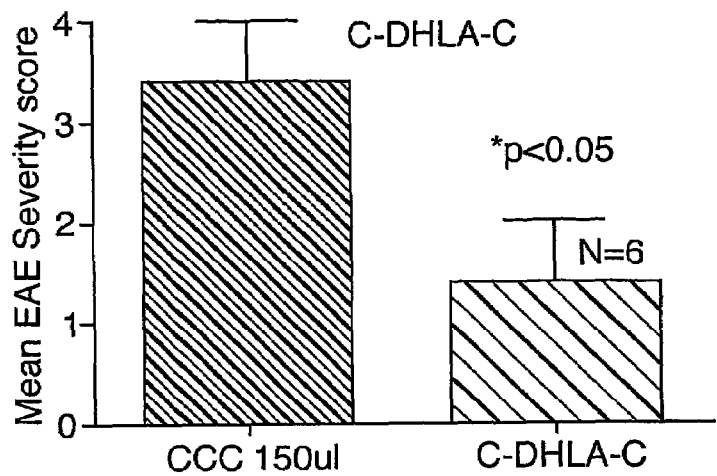
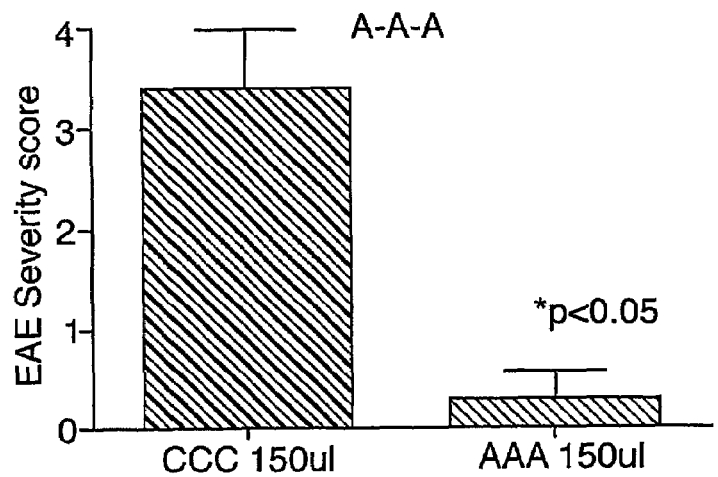
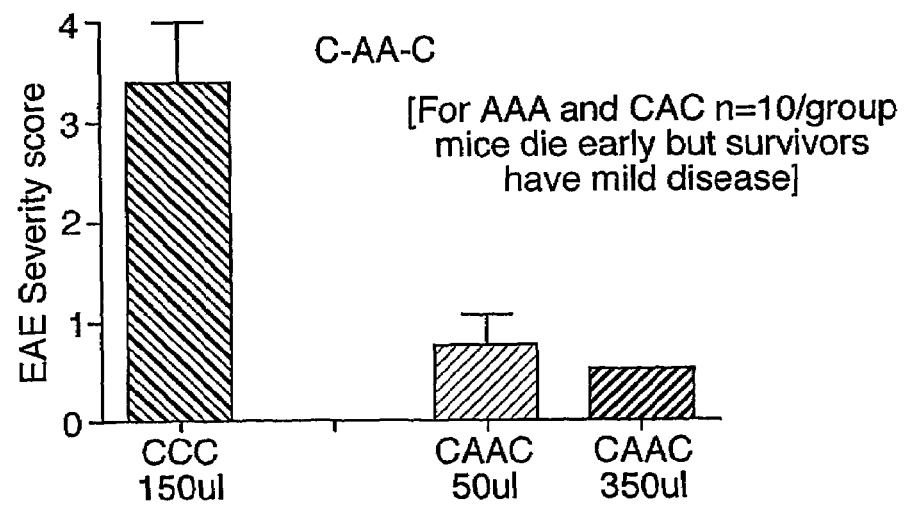

Study 6. MOG EAE in C57BL Mice

[For AAA and CAC n=10/group, mice die early but surviving mice have mild disease]

MOG EAE C57BL MICE

Test of SN-2 Principle

TREATMENT OF NEURODEGENERATIVE CONDITIONS

This application is the U.S. National Phase of International Application PCT/GB04/003524, filed 13 Aug. 2004, which designated the U.S. PCT/GB04/003524 claims priority to British Application Nos. 0319358.8 filed 18 Aug. 2003 and 0410846.0 filed 14 May 2004. The entire content of these applications are incorporated herein by reference.

The present invention relates to a method for treating neurodegenerative conditions, particularly those in which increase in transforming growth factor β (TGF-β) is beneficial, particularly TGF-β1. More particularly the present invention provides treatment for neurodegenerative conditions, particularly those such as demyelinating diseases, such as multiple sclerosis, Alzheimer's and Parkinsons diseases and the degenerative sequelae associated with head trauma, stroke and intracranial bleeds, whereby neuronal function may be improved or restored from an impaired condition, eg. by remyeleination.

Further provided are novel use of known and novel compounds comprising unsaturated fatty acid moieties for the manufacture of medicaments capable of effectively treating such conditions, more particularly being capable of achieving previously unattained levels of success with regard to recovery of neurological function.

The inventor's copending unpublished patent application PCT/GB04/002089, incorporated herein by reference, relates to the use of plant and fungal oils for the treatment of neurodegenerative diseases. These oils have high percentages of the essential fatty acid γ-linolenic acid (GLA) at the sn-2 position of their lipids, typically being over 40% of the sn-2 fatty acid total of the oil.

It is well reported in the literature that essential fatty acids (EFAs) of the n-3 and n-6 unsaturation pattern have beneficial effect in a wide variety of human physiological disorders, including autoimmune disease (WO 02/02105). Harbige (1998) Proc. Nut. Soc. 57, 555-562 reviewed the supplementation of diet with n-3 and n-6 acids in autoimmune disease states, and particularly noted evidence of benefit of γ-linolenic (GLA) and/or linoleic acid (LA) rich oils.

Bates et al noted that lipid oils comprising a mixture of linoleic acid and γ-linolenic acid residues had been suggested back in 1957 to be possibly more efficacious in treating inflammation and autoimmune diseases, but found that at 3 g oil per day (Naudicelle Evening Primrose oil 7:1 LA:GLA) patients who had relapses became more ill on the trial oil than on the control.

Although the aetiology of MS remains unknown studies have shown that MS patients have higher than normal neuroantigen autoreactive T-cells levels. These T-cells react inter alia to myelin basic protein (MBP) and myelin oligodendrocyte glycoprotein MOG) and are in an increased state of activation compared with healthy controls. The actual processes of axonal damage e.g. chronic inflammation, demyelination and astrogliosis in MS is complex but white matter inflammation and demyelination are considered to determine disease severity, whilst recent studies suggested that axonal damage in MS begins in the early stages of the disease and contributes to disability (De Stefano et al, 2001).

Experimental autoimmune encephalomyelitis (EAE) is the most frequently used animal model for immune mediated effects of MS. Studies in the guinea-pig have shown that linoleic acid partially suppresses the incidence and severity of EAE (Meade et al (1978)). (Harbige et al (1995), 1997b) demonstrated disease modifying effects of linoleic acid and γ-linolenic acid on clinical and histopathological manifestations of EAE. Depending on dose, γ-linolenic acid was fully protective in acute rat EAE whereas linoleic acid had dose-dependent action on the clinical severity but did not abolish it.

Despite these experimental findings, it is recognised that the human disease, multiple sclerosis, is highly complex and can be conversely exacerbated and ameliorated by the activity of T-cells and other immune response factors. It is thought that the n-6 fatty acids promote autoimmune and inflammatory disease based upon results obtained with linoleic acid only. TGF-β1 and PGE$_2$ production has been shown to be increased non-specifically in γ-linolenic acid fed mice ex vivo. TGF-β1 has been reported to protect in acute and relapsing EAE ((Racke et al (1993); Santambrogio et al (1993)), and PG inhibitors such as indomethacin augment, and thus worsen, the disease (Ovadia & Paterson (1982)).

Cytokines are implicated in the pathogenesis of MS, with many studies showing an increase in myelinotoxic inflammatory cytokines (TNF-α, IL-1β and IFN-γ) coinciding with the relapse phase of the disease. Conversely, levels of the anti-inflammatory and immunosuppressive cytokine transforming growth factor-beta1 TGF-β1) appear to be reduced during a phase of relapse and increase as the patient enters remission. Thus the balance between biologically active TGF-β1 and the pro-inflammatory TNF-α, IL-1β and IFN-γ appears to be dysregulated during MS relapse-remission.

During natural recovery phase from EAE, TGF-β1-secreting T-cells inhibit EAE effector cells, TGF-β1 is expressed in the CNS and, in oral-tolerance-induced protection in EAE, TGF-β and PGE$_2$ are expressed in the brain (Karpus & Swanborg (1991); Khoury et al (1992)). Harbige ((1998) concluded that dietary γ-linolenic acid effects on EAE are mediated through Th$_3$-like mechanisms involving TGF-β1 and possibly through superoxide dismutase antioxidant activity.

Borage oil (typically 20% to 23% γ-linolenic acid and 34 to 40% linoleic acid per 100% fatty acid content) and *Mucor javanicus* fungal oil (see FIG. 1) have been shown to be effective in the EAE animal model used to identify MS candidates, whilst never having been shown to be significantly effective in the human disease. High levels of linoleic rich oil containing low levels of γ-linolenic acid (EPO: linoleic acid: γ-linolenic acid 7:1) partially suppressed the incidence and severity of EAE in rat (Mertin & Stackpoole, 1978) whereas the Bates' Naudicelle study referred to above led to worsening of patients. In spite of the use of Borage oil and other GLA/LA containing oils such as Evening Primrose oil by multiple sclerosis sufferers over the past 30 years or so, the vast majority of patients fail to recover from the disease, showing no significant improvement, with the underlying disease continuing to progress to death.

It has been suggested to use, inter alia, γ-linolenic acid and linoleic acid rich Borage oil as a means to provide immunosuppression in multiple sclerosis (U.S. Pat. No. 4,058,594). Critially, the dose suggested is 2.4 grams of oil per day and no actual evidence of efficacy is provided. This is much lower than the low 5 g/day dose found to be ineffective in vivo in man in the PCT/GB04/002089 study.

Other more dramatic immunosuppressant treatments, including T cell depleters and modulators such as cyclophosphamide, are also shown to be effective in the EAE model, but where these are employed in the human multiple sclerosis disease symptoms improve, but the underlying disease continues to progress. T-cells indeed produce beneficial cytokines, such as TGF-β1, as well as deleterious ones in man. David Baker of Institute of Neurology, UK summed up the disparity between what is effective in the EAE and in MS with a paper entitled 'Everything stops EAE, nothing stops MS' at the 10th May 2004 UK MS Frontiers meeting of the UK MS Society.

It is clear that immunosuppression alone cannot cure MS. This is almost certainly due to a fundamental underlying metabolic disorder in MS patients, in addition to the autoimmune disease, that leads to membrane abnormality, cytokine dysregulation and subsequent immune attack and lesioning. Although patients go into remission in relapse-remitting disease, the underlying demyelination proceeds.

The 'gold standard' treatment for MS remains interferon, such as with β-Avonex®, Rebif® and other interferon preparations. This gold standard treatment only addresses needs of some, eg 30%, of the patients and even in these symptom improvement is restricted to reduced severity of relapses. Whilst symptoms may be reduced in a proportion of patients, the disease tends to progress to further disability and death due to underlying degeneration.

In their as yet unpublished PCT/GB04/002089 study the present inventors have surprisingly determined that with compliance to a 'high dose' treatment with triglyceride oil containing high levels of sn-2 γ-linolenic acid (>40% of residues at the sn-2 being of γ-linolenic acid) with suitable accompanying fatty acid content, remarkable levels of improvement in almost all symptoms of MS can be achieved, way surpassing that provided by the current gold standard treatment. Such success is particularly surprising in the light of the prior use of other γ-linolenic acid containing preparations without success, such as the Naudicelle study.

The PCT/GB04/002089 study shows that over an 18-month period, patients taking high dose (15 g/day) selected high sn-2 γ-linolenic acid borage oil showed significant ($p<0.001$) and marked improvements in EDSS score, a reduced rate of relapse, symptomatic relief of muscle spasticity and painful sensory symptoms, and improved objective measures of cognitive functions. Low doses of 5 g/day of this borage oil were without effect.

Patients taking the highest dose of this borage oil maintained their level of peripheral blood mononuclear cell production (PBMC) of TGF-β1 during the trial period, their pro-inflammatory cytokines TNF-α and IL-1β were significantly and markedly (<70%) reduced and they either maintained or increased the PBMC membrane long chain omega-6 fatty acids dihomo-γ-linolenic acid (DHLA) and arachidonic acid (AA) in contrast to patients taking placebo who demonstrated loss of these fatty acids over the course of the trial period.

This whilst immuno-suppression would be expected to reduce increase of active lesioning and neurodegeneration, the high sn-2 GLA oil treatment apparently targeted maintenance and/or increase of key membrane lipid components that are otherwise specifically lost in MS, being consistent with a correction of a metabolic defect not otherwise effectively treated by current therapies. The fact that the low dose (5 grams/day) had no effect on this supports such determination.

γ-Linolenic acid (18:3n-6, or GLA) is known to be rapidly converted to longer-chain omega-6 polyunsaturated fatty acids dihomo-γ-linolenic acid and arachidonic acid in vivo (Phylactos et al 1994, Harbige et al 1995, 2000). Therefore to determine how to increase the level of membrane long chain omega-6 fatty acids in MS the inventors have reviewed their results obtained with several GLA-containing oils:—both fungal (from *Mucor javanicus*) and plant (*Borago officianalis*), Evening primrose *Oenothera* spp. or Blackcurrant *Ribes* spp) as well as a synthetic tri-GLA oil as GLA delivery systems in an in vivo experimental animal model of MS known as chronic relapsing experimental autoimmune encephalomyelitis (CREAE).

Induction of EAE in rats does not produce histological features of demyelination (Brosnan et al 1988) but induces an acute mono-phasic disease pattern, unlike MS which is characterised by CNS demyelination and is in the majority of cases clinically relapsing-remitting. Chronic relapsing and demyelinating EAE models (CREAE) however are characterised by demyelination and relapse phases. With the demonstration that myelin oligodendrocyte glycoprotein (MOG) is an important neuroantigenic target in MS (Genain et al 1999) and the demonstration of far greater responses of peripheral blood auto-reactive lymphocytes to this neuroantigen, compared with MBP, in MS (Kerlero de Rosbo et al 1993, 1997) MOG induced CREAE has become the animal model of choice with features closely resembling those observed in MS (Fazakerely et al 1997, Genain et al 1999, Amor et al 1994).

Evidence from the inventor's CREAE and rat EAE feeding studies indicates that an enriched blackcurrant seed oil (72% w/w 18:3n-6, GLA) did not protect against EAE (see Table 3). Importantly blackcurrant seed oil has a low sn-2 GLA with most of the GLA in the sn-1 and sn-3 positions (Lawson and Hughes 1988). Furthermore a structured triacylgcerol containing three GLA moieties (TG-GLA) provided protective effects similar to that of the borage oil used in CREAE (Table 2). This would also be consistent with the sn-2 GLA being important i.e. the outer pair sn-1 and sn-3 GLA being enzymatically removed in vivo and probably undergoing oxidation leaving the sn-2 GLA only. This selective hydrolysis arises from the known ability of specific lipases to remove the sn-1 and sn-3 fatty acids from triacylglycerol molecules but an apparent protection of the sn-2 position in vivo (Lawson and Hughes 1988, Kyle 1990).

This review has led the inventors to postulate that glycerides having sn-2-γ-linolenic acid, dihomo-γ-linolenic acid or arachidonic acid residues will be superior in correcting MS metabolism even to the high sn-2-γ-linolenic acid Borage oil of their earlier trial. This would allow lower doses of lipid to be taken and/or possibly decrease the time of treatment which would result in beneficial effect.

Table 3 of EP 0520624 (Efamol Holdings) compares the triglyceride content of Evening Primrose and Borage Oils, the former being taught to be more therapeutically effective than the latter for a variety of GLA responsive disorders. This document indicates Borage oil to have twenty seven different trigyceride components, only 20% of which have sn-2 GLA. Page 3, lines 40-42 notes that biological testing has shown that equal amounts of GLA may indeed have very different effects when that GLA is supplied as different oil sources. Crucially, it then directs the reader to one particular fraction present in Evening Primrose Oil (EPO), but not Borage Oil, as being responsible for the former's superior effect in raising PGE1 (see EP 0520624 Chart page 4 and Table 2) and thus anti-inflammatory effect: that fraction being identified as di-linoeoyl-mono-gamma-linolenyl-glycerol (DLMG) which it states to be 18 to 19% of the total triglyceride in EPO. Critically, page 6 clearly teaches that the position of the GLA, in sn-1, 2 or 3, is not important to this effect.

Dines et al (1994) Proceedings of the Physiological Society, Aberdeen Meeting 14-16 Sep. 1994 report on studies of treatment of diabetic neuropathy neuronal damage with γ-linolenic acid containing oils of the type advocated by EP 0520624 and again note that Borage Oil was not very effective in treating this neurodegeneration whereas Evening primrose oil was. The paper concludes that Borage Oil contains other constituents that interfere with GLA activity.

The present inventors now set out, in view of their results for high sn-2-γ-linolenic acid Borage Oil, to demonstrate that it is indeed the presence of an sn-2-γ-linolenic acid, dihomo-γ-linolenic acid or arachidonic acid residue in a glyceride, particularly a triglyceride, that gives it efficacy in treating EAE, CREAE and the human disease MS.

In a first aspect the present invention provides a method of treating a patient in need of therapy for a neurodegenerative disease comprising administering to that patient a therapeutically effective dose of a defined structure lipid glyceride comprising a glycerol moiety esterifed with one or more fatty acid moieties, characterised in that the lipid has a fatty acid moiety at the sn-2 position selected from the group of residues consisting of residues of γ-linolenic acid, dihomo-γ-linolenic acid and arachidonic acid.

Particularly advantageously treated neurodegenerative diseases are those involving demyelination. The present method specifically arrests underlying neurodegeneration and restores neuronal function. Particularly the method normalises neuronal membrane composition, and restores healthy PBMC spontaneuosly released TGF-β1/TNFα ratios and the ratios of TGF-β1 with other PBMC released cytokines. Most advantageously the method arrests neurodegeneration in multiple sclerosis of all types but particularly relapsing remitting, primary progressive and chronic progressive MS and the restoration, in part or completely, of neuronal function such as measured, eg. By MRI or CAT scan or by EDSS score. Such method may also be used in treatment of cerebral impairment after stroke, head trauma and intracranial bleeding where there is demyelination or neuronal damage. Further application is provided in treating other chronic demyelination such as in Alzheimer's and Parkinson's disease.

Preferably the lipid is administered for a duration and at a dose sufficient to maintain or elevate TGF-β levels in the patient to therapeutic levels. By therapeutic levels is meant levels at least consistent with healthy subjects. Preferably the dose is such as to produce a TGF-β1/TNF-α ratio spontaneously released from peripheral blood mononuclear cells (PBMCs) isolated from blood of a patient, after 18 months of daily dosing, of 0.4 to 3.0, at least 0.5, more preferably at least 0.75 and most preferably at least 1. Preferably the dose is such as to produce a TGF-β1/IL-1β ratio in blood of a patient, after 18 months of daily dosing, of at least 0.5, more preferably at least 0.75 and most preferably at least 1. Preferably said levels are produced after 12 months and more preferably after 6 months.

Typically the amount of lipid administered daily will be between 0.5 and 30 grams, orally dosed, still more preferably between 1 and 20 grams and most preferably between 1 and 18 grams, typically 3 to 5 grams.

Where the sn-2 moiety is that of a γ-linolenic acid residue, the dose may be toward the higher end of these ranges, particularly where the sn-1 and sn-3 moieties are relatively inert, eg. being metabolically utilised acids such as saturated fatty acids. Where the sn-2 moiety is that of a dihomo-γ-linolenic acid residue, the dose may be less, whilst where the sn-2 moiety is that of an aracidonic acid residue, efficacy is higher, but dosing should be more cautious, due to possibilities of unwanted side effects at higher levels.

More preferably the method is characterised in that the lipid is a monoglyceride, diglyceride or triglyceride containing the at least one sn-2 γ-linolenic acid, dihomo-γ-linolenic acid or arachidonic acid moiety of general Formula I below:

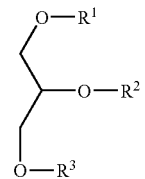

Formula I wherein $R^1$ and $R^3$ are independently selected from hydrogen and acyl groups, and $R^2$ is selected from the group consisting of γ-linolenic acid, dihomo-γ-linolenic acid and arachidonic acid residues.

For the purpose of the present invention acyl groups are defined as comprising at least one carbonyl group on the end of an optionally substituted hydrocarbyl chain selected from alkyl and alkenyl chains, the carbonyl group being directly attached by its carbon to the oxygen of the glycerol residue shown in Formula 1.

Preferred acyl groups $R^1$ and $R^3$ are saturated fatty acid moities of formula $-CO-(CH_2)_n-CH_3$, wherein n is an integer selected from 1 to 22, more preferably being 4 to 16, still more preferably being from 5 to 12, most preferably being from 6 to 10. Particularly preferred acyl groups are those of caprylic and capric acids, particularly being 1,3-dicaprylic or 1,3-dicapric glycerols having the γ-linolenic acid, dihomo-γ-linolenic acid or arachidonic acid moiety at the sn-2 position.

Preferred glycerides for use in the invention are triglycerides.

U.S. Pat. No. 4,701,469 describes some potential triglycerides for nutraceutical use that the present inventors have determined may be used in the method of the invention, although it only specifically describes 1,3-dioctanyl triglycerides wherein the sn-2 acid is of an EFA, only 1,3-dioctanoyl eicosapenta glycerol is described as having been prepared. These are said to useful in inter alia immunomodulation, but although a number of diseases are specified, use in immunosupresion in neurodegeneration and MS are not listed.

Whilst most preferred groups $R^1$ to $R^3$ for inclusion in the compound of formula I are simple saturated fatty acids or naturally occurring fatty acids with structural or metabolic function, such as medium chain or long chain fatty acids, there are other possibilities. Particularly preferred fatty acids are those that are utilised primarily by the metabolism for producing energy. Where fatty acids are structural, that is utilised in membranes, they are conveniently such as γ-linolenic acid, linoleic acid, dihomo-γ-linolenic acid and arachidonic acid residues. By residue is meant the moiety that remains after the fatty acid carboxyl group esterifies to one of the hydroxy groups of the glycerol molecule.

Other preferred acids for sn-1 and sn-3 are selected from fatty acids that are metabolised in the human to yield energy as opposed to a fatty acid that is primarily directed to the structural membrane pool: such preferred acids include oleic acid and palmitic acid.

Where the sn-1 and sn-3 fatty acid chain ($R^1$ and $R^3$) is unsaturated it may also be that of other essential fatty acids, such as the n-3 acids such as stearidonic acid, eicosapentanoic acid and docosahyexanoic acid. Where the fatty acid is optionally substituted these will preferably be by hydroxy, oxo, carboxyl, alkyl, alkenyl and alkoxy groups. The hydrocarbyl chain is preferably one of from 1 to 30 carbon atoms in length, more preferably from 4 to 28 carbon atoms in length, still more preferably 4 to 24 carbon atoms in length. Most preferably the hydrocarbyl chain is that of a fatty acid, more particularly a mono or polyunsaturated fatty acid.

Many of the preferred lipids for use in the method of the invention are known and may be prepared by chemical process known in the art. For example, many are commercially available, such as trigamma-linolenin, known as TLG, but herein referred to as GGG, reflecting the identity of groups $R^1R^2R^3$ where G represents γ-linolenic acid residues.

GGG is commercially available from Nu-Check-Prep Inc. EP 0300844 describes its synthesis using a base-catalysed trans-esterification of triacetin with methyl gamma linolenate to give a mixture containing 80% GGG, unreacted methyl γ-linolenate and 10% mono- and di-glycerides.

Triarachidin is known and small quantities can be obtained commercially eg. from Sigma AAA has been synthesised from arachidonic acid by using immobilised lipase patented for angiogenisis-enhancing activity U.S. Pat. No. 4,888,324.

However, whilst the tri and di-γ-linolenic acid, dihomo-γ-linolenic acid or arachidonic acid di or triglycerides may be used, the present inventors prefer the use of the mono-γ-linolenic acid, dihomo-γ-linolenic acid or arachidonic acid sn-2 ester triglycerides because they administer less of the immunomodulatory and proinflammatory fatty acids γ-linolenic acid, dihomo-γ-linolenic acid or arachidonic acid whilst retaining the enhanced activity that the sn-2 γ-linolenic acid, dihomo-γ-linolenic acid or arachidonic acid moiety provides with regard to the desired membrane normalising and disease modifying effect.

Novel lipids which are preferred are accessible by processes and methods set out in the Examples herein. Most preferred lipids are those where there is just a single γ-linolenic acid, dihomo-γ-linolenic acid or arachidonic acid moiety esterified to the glycerol at sn-2, with the flanking sn-1 and sn-3 acids being unsaturated medium chain or long chain acids.

Thus a further aspect of the present invention provides novel lipids disclosed herein including compounds of formula II

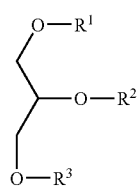

wherein $R^1$ and $R^3$ are the same and are —C(O)(CH$_2$)$_n$CH$_3$ wherein n is selected from 4 to 14, more preferably 6 to 10 and most preferably 7, 8 or 9 and $R^2$ is selected from γ-linolenyl, dihomo-γ-linolenyl and arachidonyl.

A further aspect of the present invention provides a method for synthesis of a compound of general formula III

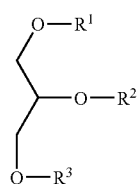

wherein $R^1$ and $R^3$ are the same and are —C(O)(CH$_2$)$_n$CH$_3$ wherein n is selected from 4 to 14, more preferably 6 to 10 and most preferably 7, 8 or 9 and $R^2$ is γ-linolenyl residue, dihomo-γ-linolenyl residue or arachidonyl residue comprising reacting 1,3-dihydroxyacetone with a compound of formula X—C(O)(CH$_2$)$_n$CH$_3$ wherein X is selected from Cl, Br and I, to give the corresponding 1,3-di-(C(O)(CH$_2$)$_n$CH$_3$)2-keto compound reducing the keto group to the corresponding 1,3-di-(C(O)(CH$_2$)$_n$CH$_3$)2-ol and reacting that with γ-linolenyl chloride or dihomo-γ-linolenyl chloride or arachidonyl chloride.

A still further aspect of the present invention provides a method for synthesis of a compound of general formula IV

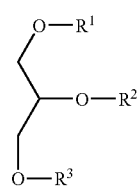

wherein $R^1$ to $R^3$ are the same and selected from γ-linolenyl residue, dihomo-γ-linolenyl residue or arachidonyl residue comprising reacting the corresponding γ-linolenyl chloride, dihomo-γ-linolenyl chloride or arachidonyl chloride with glycerol.

Synthesis of some of these compounds is described below and schemes shown in the figures below.

For example, a single-step esterification of glycerol using GLA and a coupling agent, such as DCCI/DMAP (1,1-Dicylcohexylcarbodiimide/4-dimethylaminopyridine) coupling reagents may be carried out. This method gives a good yield but generates impurities that, unless removed, make the final oil cloudy. This may be circumvented by using a coupling agent such as EDCI (1-(3-dimethylaminopropyl)-3-ethylcarbodiimide hydrochloride) which gives rise to water-soluble by-products that are easier to remove. Jpn. Kokai Tokkyo Koho JP 05310638 A2 22 Nov. 1993 Heisei, 6 pp. describes the preparation of tri-α-linolenin (LnLnLn where Ln is linoleic acid) using DCCl, and analogous but different reaction.

A alternative approach provides a two-step sequence that utilises reaction of GLA-Cl (prepared from γ-linolenic acid and oxalyl chloride) and glycerol in dichloromethane/pyridine with good yields at scale-up to 250 g purified by column chromatography. Jpn. Kokai Tokkyo Koho JP 04328199 A2 17 Nov. 1992 Heisei, 5 pp. (Japan) Concentration of a-linolenic acid triglyceride by flash chromatography. Ando, Yukiki, Watanebe, Yoichi, Takagi, Yoshiaki (Nisshin Oil Mills Ltd, Japan) describes a related but different technique for purification of tri-α-linolenin (LnLn).

Comparative example tricaprin (glycerol tridecanate) is a known compound commercially available from Sigma. It has been prepared by reaction of methyl decanoate and sodium glyceroxide with subsequent purification of the crude product by column chromatography (see E. S. Lutton and A. J. Fehl, *Lipids*, 5, 90-99 (1970))

An alternative method involves the acid-catalysed reaction of glycerol with decanoic acid followed by four crystallisations (see L. H. Jenson and A. J. Mabis, *Acta Cryst.*, 21, 770 (1966)).

The applicant further provides an improved process which allows glycerol to react with more than 3 equivalents of decanoyl chloride and purified the tricaprin product by recrystallisation.

Further aspects of the present invention provide use of triglyceride oils as described above for the manufacture of a medicament for the treatment of neurodegenerative diseases as set out for the method of the invention. Particularly preferred medicaments are for the arresting and reversing of neurodegeneration in multiple sclerosis of all types but particularly relapsing remitting, primary progressive and chronic progressive and the restoration, in part or completely, of neuronal integrity function such as measured, eg. By MRI or CAT scan or by EDSS score. Other TGF-β1 responsive diseases may be treated as set out previously.

The lipids for use in the present invention may be administered by any of the conventional vehicles known in pharmacy. Most conveniently they are administered as neat oils or in admixture with foodstuffs, in the form of capsules containing such oils, or in enterically coated forms. Other forms will occur to those skilled in the art but Remington Pharmaceutical Sciences 19$^{th}$ Edition.

It will be realised by those skilled in the art that other beneficial agents may be combined with the lipids for use in the present invention or otherwise form part of a treatment regime with the lipids. These might be ion channel blockers, eg. sodium channel blockers, interferons (α, β, or γ), T-cell depleters, steroids or other palliative agents. It will further be realsied that where the immune and inflammatory responses are being modulated, such combinations will need to be made carefully, given the complex nature of these systems. However, given the delayed response to the present oils, shorter acting agents might be beneficial in the first months of treatment before the TGF-β1 levels are normalised, as long as the additional treatment does not impede this normalization process.

The synthesis of structured lipids for use in the present invention is described below together with synthesis of comparative examples. Some of these lipids are novel while others are known but have not been used for the treatment of the invention.

The present invention will now be described by way of Example only by reference to the following non-limiting Tables, Examples and Figures. Further embodiments falling within the scope of the invention will occur to those skilled in the art in the light of these.

TABLES

Table 1: Shows the compositional % Total fatty acid content of various triglyceride oils and protective effect in EAE.

Table 2: Shows the parameters of the three treatment groups in high sn-2 GLA Borage Oil trial described in PCT/GB04/002089.

Table 3: Shows the effect of various forms of GLA on EAE incidence and clinical score in SJL mice: lower score indicating improved therapeutic effect.

Table 4: Shows the failure of enriched Blackcurrent oil, a high GLA, but low sn-2-GLA, plant oil, to match fungal and Borage oils in EAE.

FIGURES

FIG. 1: Shows spontaneous peripheral blood mononuclear cell cytokine production in placebo and high sn-2 γ-linolenic acid, PCT/GB04/002089 trial oil treated human MS patients at 18 months.

FIG. 2: Shows the effect of placebo and low dose (5 g/day) high sn-2 GLA Borage oil on human MS patient EDSS score as compared to high dose (15 g/day) displayed as a histogram with months treatment on the x axis.

FIG. 3: Shows the effect of placebo, low dose and high dose high sn-2 GLA Borage oil on human MS patient Mean Relapse rate (%) as histogram with months on x axis.

Figure 4:
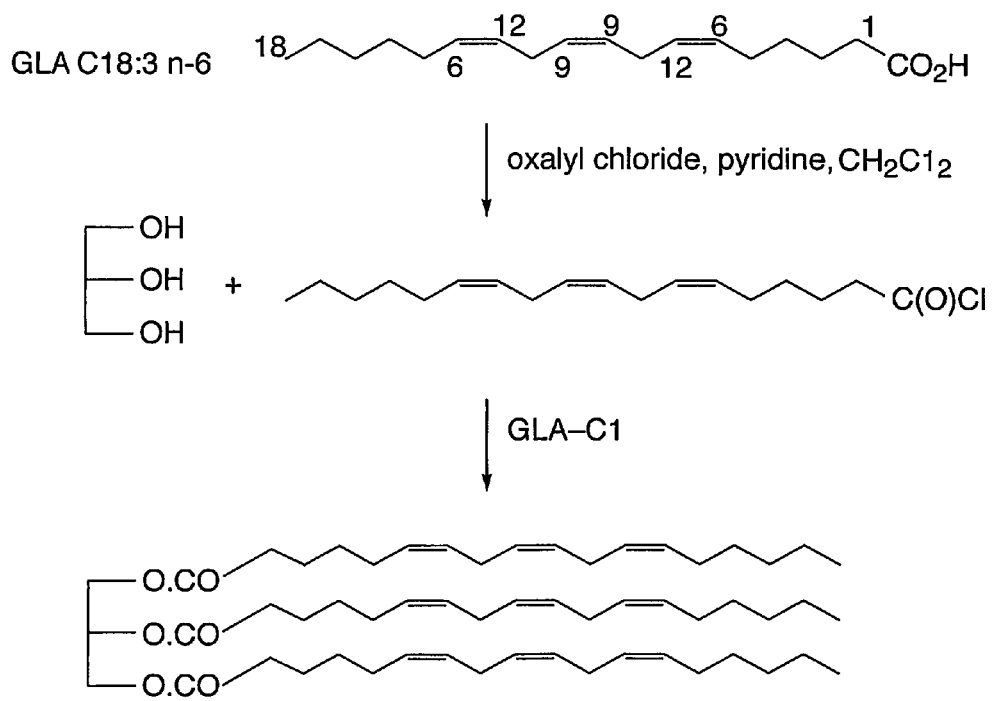

FIG. 4: Shows the reaction scheme for synthesis of a single fatty acid triacylglyceride for use in the method and use of this invention.

FIG. 5: Shows the reaction scheme for synthesis of control compound tricaprin.

Figure 6:
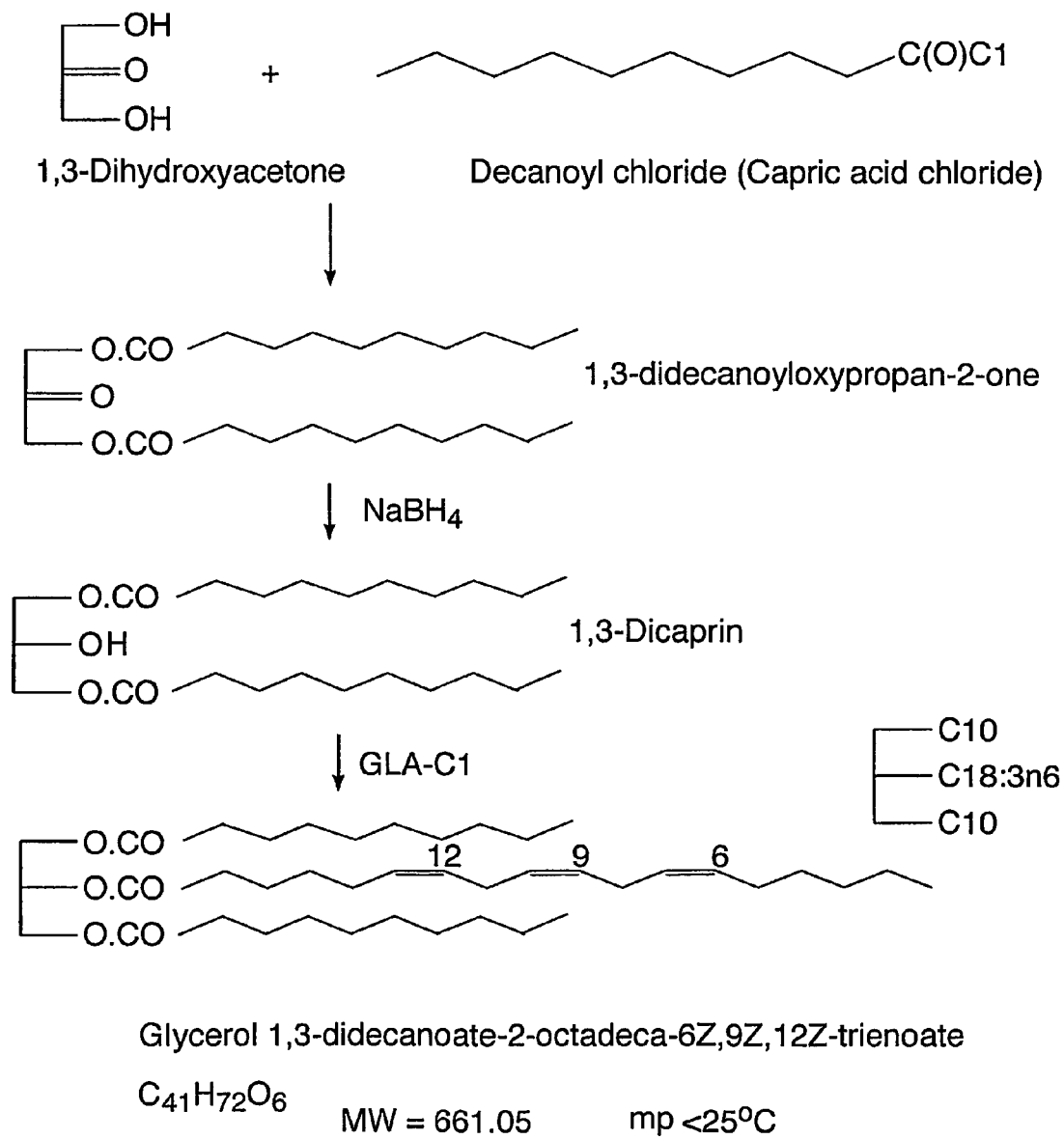

FIG. 6: Shows the reaction scheme for synthesis of CGC, a mixed fatty acid triacylglyceride of the invention.

Figure 7:
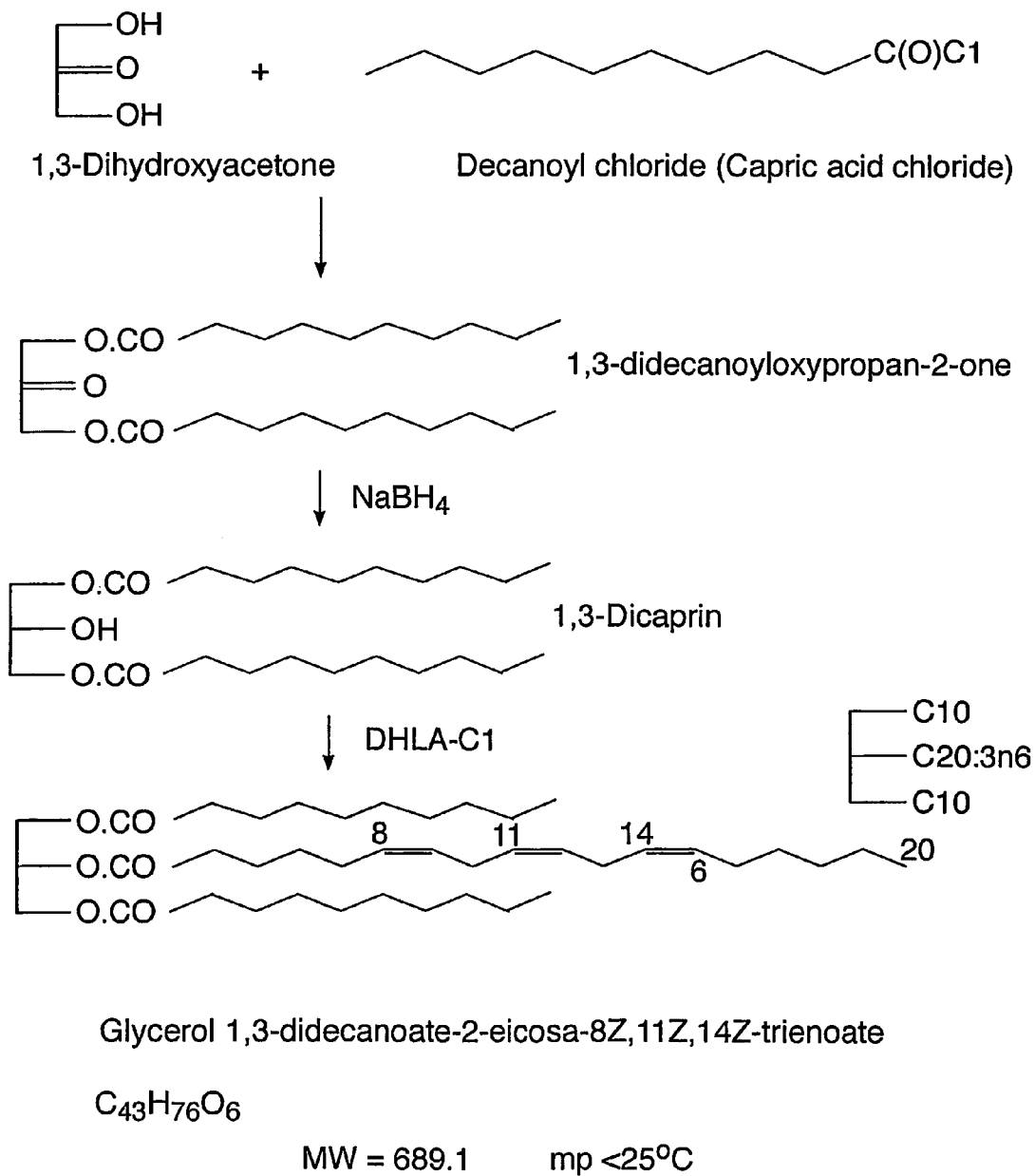

FIG. 7: Shows the reaction scheme for synthesis of C-DH-GLA-C, a mixed fatty acid triacylglyceride of the invention.

Figure 8:
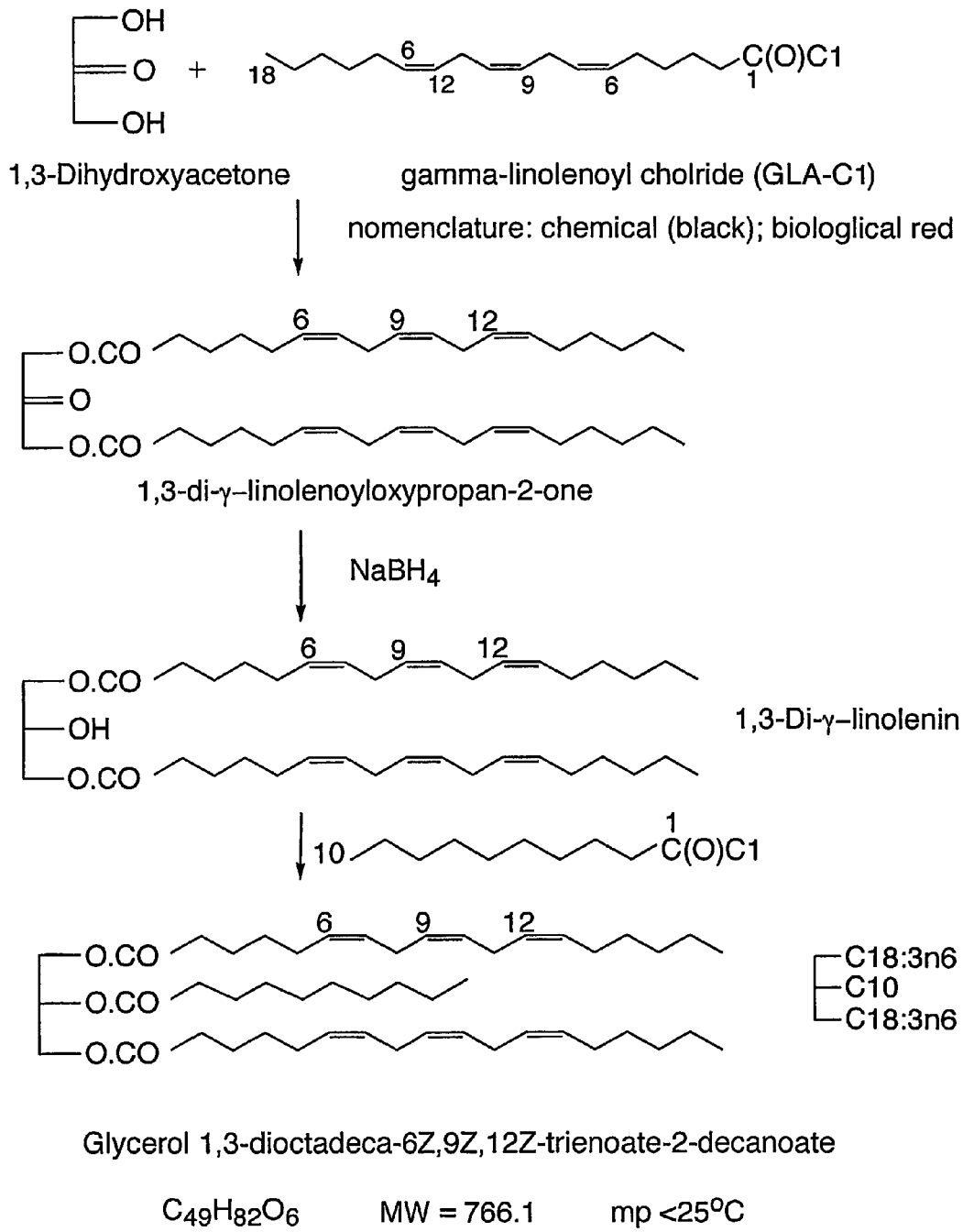

FIG. 8: Shows the reaction scheme for synthesis of control compound GCG, 1,3-dicapryl, 2-γ-linolenic acid.

Figure 9:
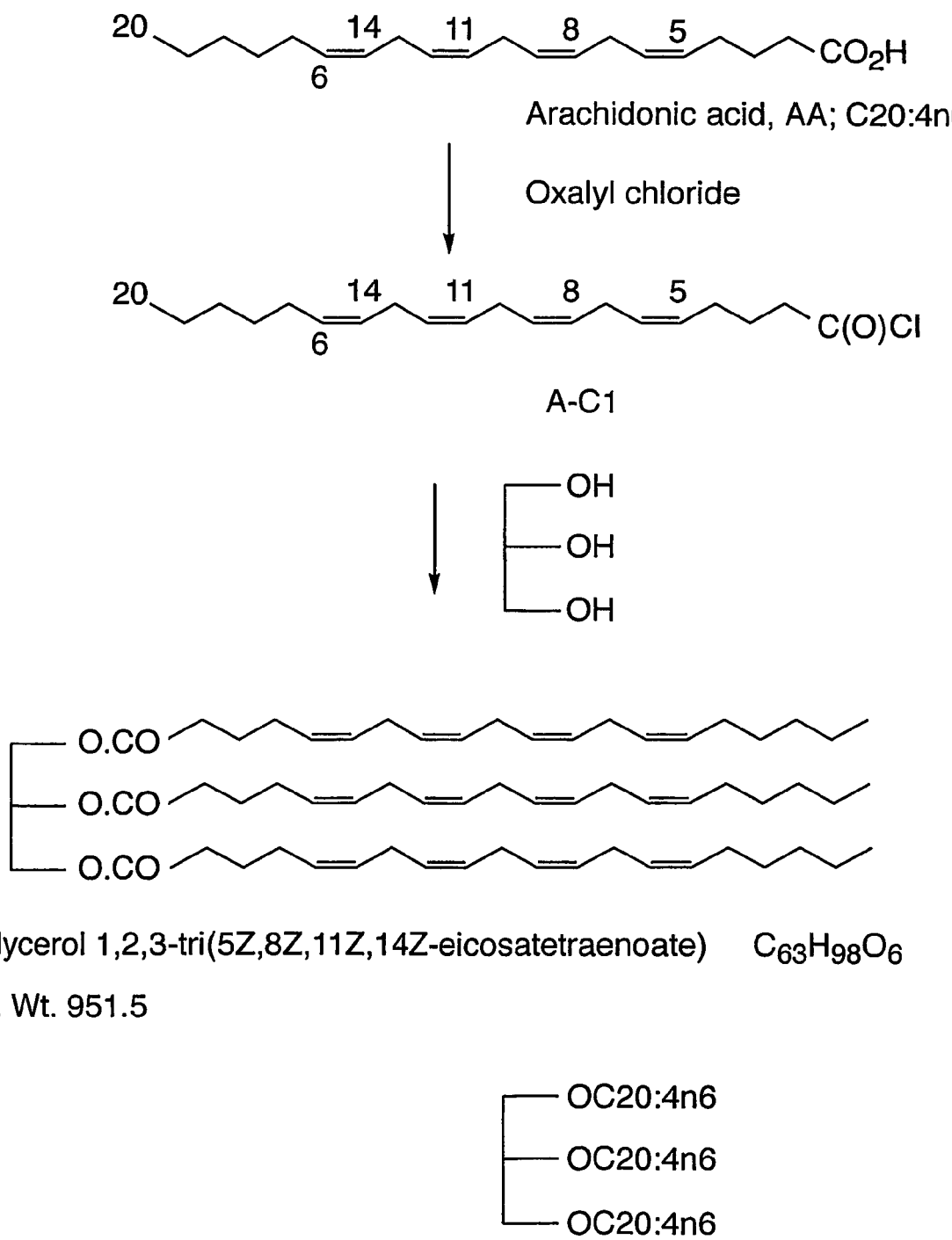
Figure 12:
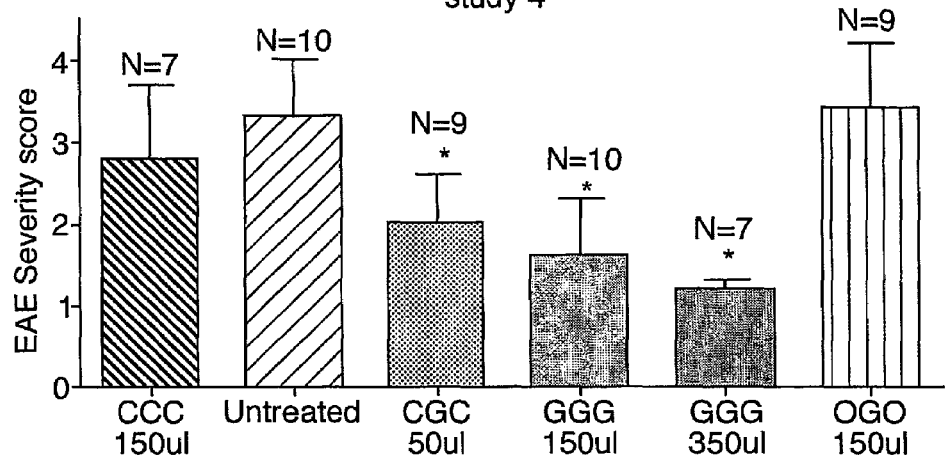
Figure 13:
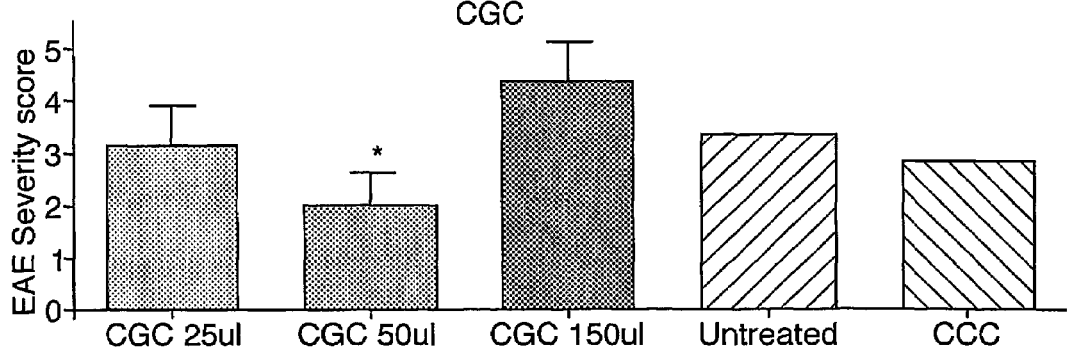
Figure 14:
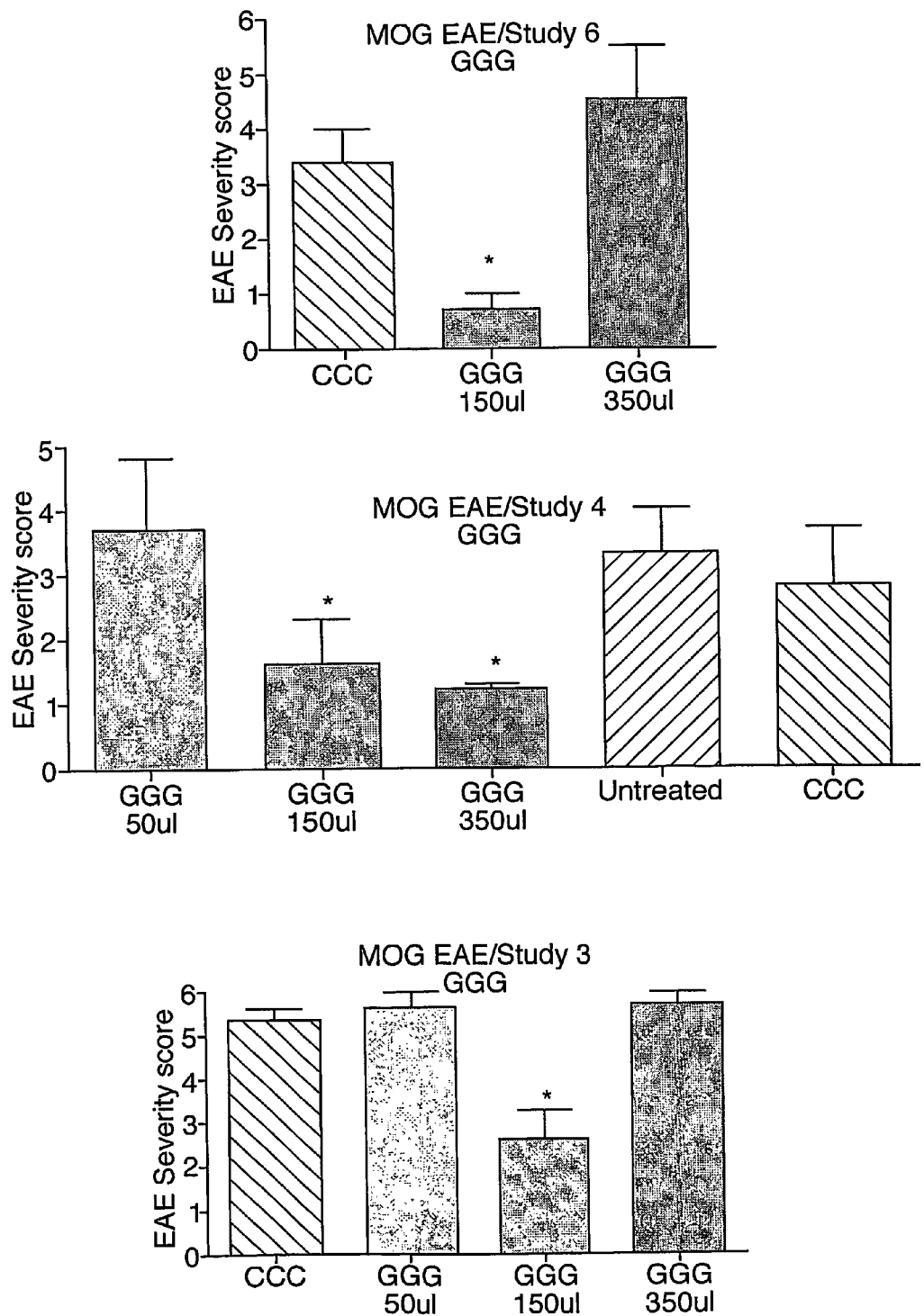
Figure 15:
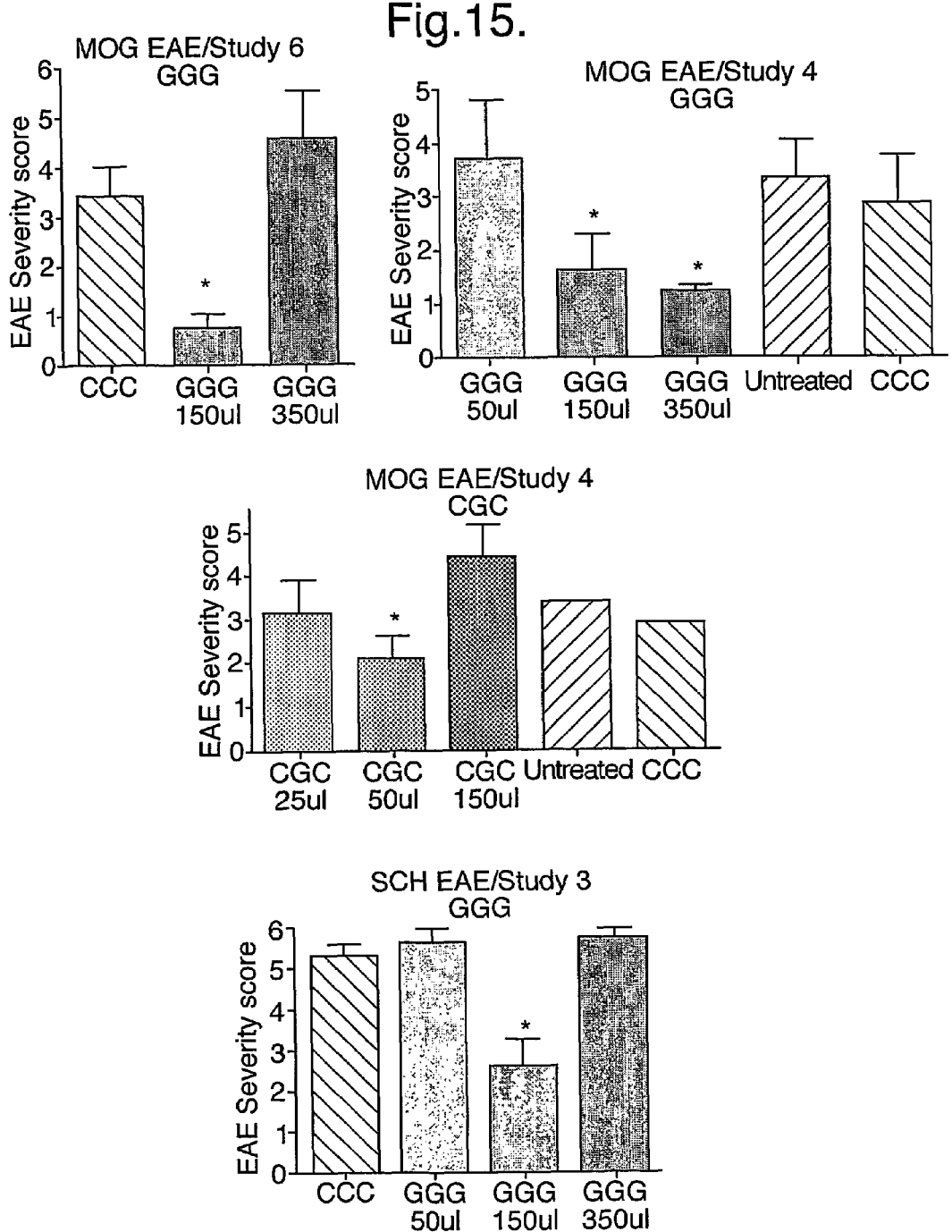
Figure 16:
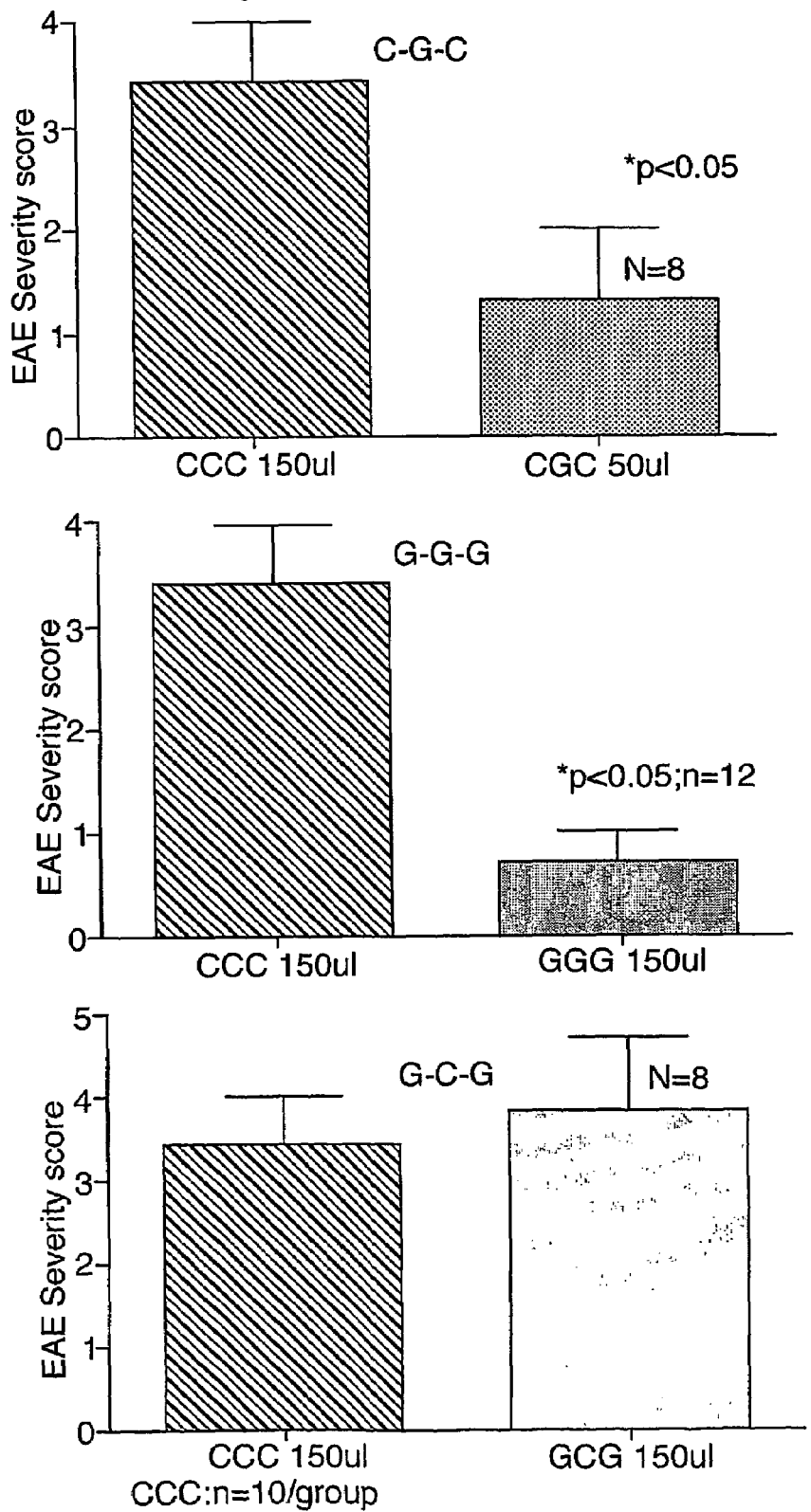
Figure 18:
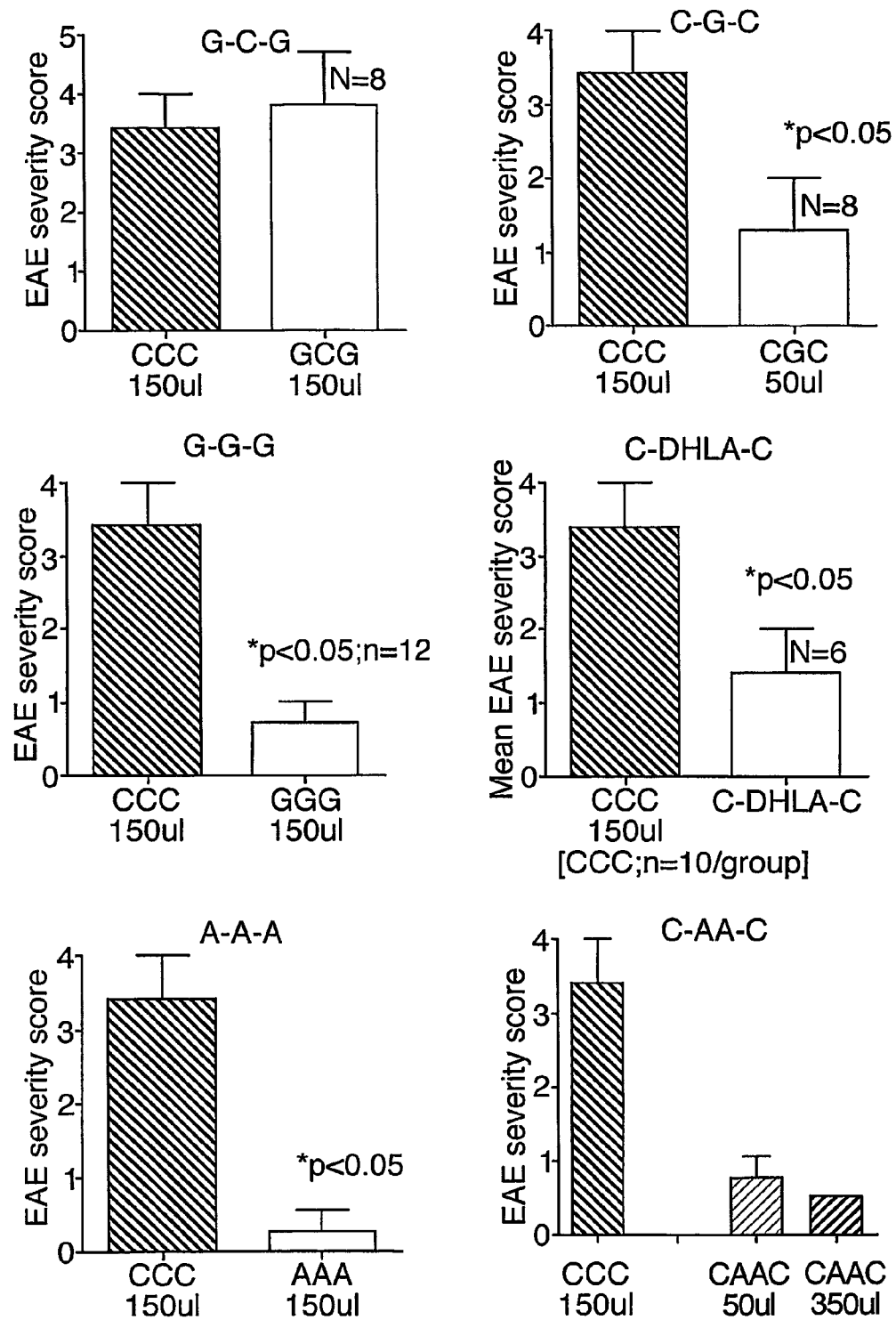
Figure 19:
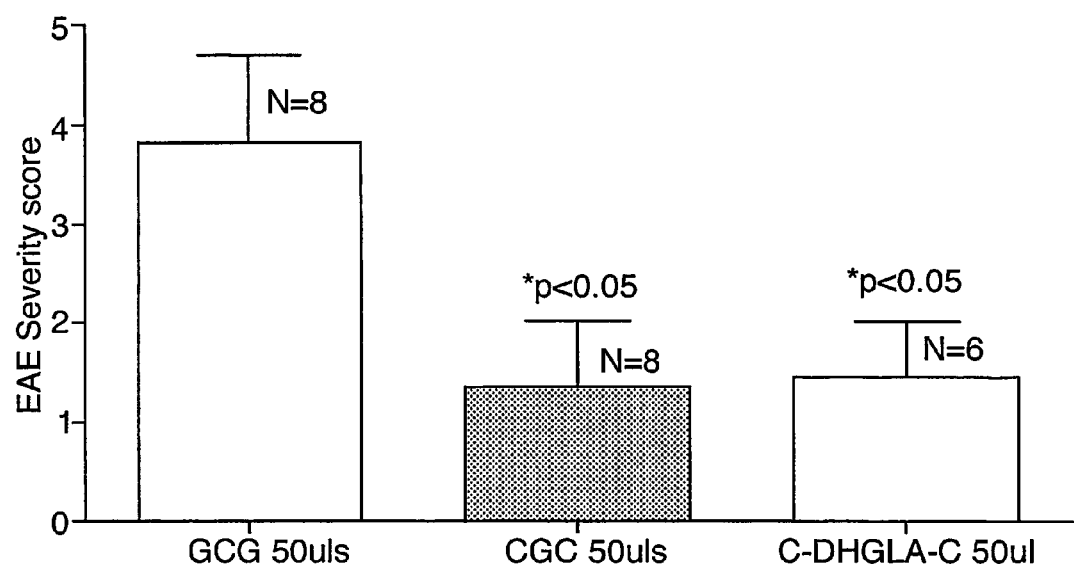

FIG. 9: Shows the reaction scheme for synthesis of C-AA-C, a mixed fatty acid traiacylglyceride of the invention.

FIG. 10 to 19 show the results of EAE studies in SJL and C57BL mice as set out in the examples below. (DHLA=DHGLA: A=AA)

EXAMPLES

High sn-2 Borage Oil (PCT/GB04/002089) Trial.

Twenty-eight active relapsing-remitting (two relapses in the preceding 18 months) multiple sclerosis patients (ages ranging from 18 to 65 yrs) were entered into a double-blind placebo controlled trial to investigate the effects of encapsulated borage oil on clinical activity and laboratory parameters over 18 months. This oil was of high sn-2 γ-linolenic (GLA) content (>40% of sn-2 residues being γ-linolenic acid) with low monene (eg. erusic acid) content and had no added Vitamin E, a known immunomodulator.

Patients were recruited from neurology out-patient clinics at two inner city hospitals; hospital informed consent was obtained on first (baseline) visit. Exclusion criteria include any form of steroid or immunosuppressive drug treatment, pregnancy, hyperlipidemia, regular use of aspirin or related drugs and vitamin or fatty acid supplementation within the previous three months.

Only patients meeting all the following criteria were included in the trial: (a) able to provide informed consent prior to treatment, with the full understanding that consent may be withdrawn at any time without prejudice; (b) male or female out-patients aged 18 to 60 years inclusive; (c) have confirmed diagnosis of clinically definite relapsing MS; (d) have had at least three documented clinical relapses in the past two years; (e) have a baseline Expanded Disability Scoring Scale (EDSS) score of 0.0-5.5 inclusive, provided they have well documented exacerbations; and (f) healthy, apart from the MS-related symptoms, as confirmed by the medical history, physical examination and clinical chemistry, urine and haematological tests.

Patients were randomly allocated by the Pharmacy Department to one of three groups each containing 12 patients:
One clinical group (n=12) to receive placebo (5 g of Polyethylene Glycol 400)
Second clinical group (n=12) to receive low-dose (5 g) refined *Borage officinalis*
Third clinical group (n=12) to receive high-dose (15 g) refined *Borage officinalis*

Supplementation was in the form of one gram oil capsules daily (5/day for low dose, 15/day high dose) for 18 months duration. *Borage officinalis* oil and omega-6 polyunsaturated fatty acids are food ingredients that are generally recognised as safe for human consumption (GRAS). There are no classification or labelling requirements under EC regulations. Clinical assessment included: Extended Disability Scale Scores (EDSS) and clinical relapse record. Venous blood (50 mls) was obtained for laboratory studies on the $1^{st}$, $3^{rd}$, $6^{th}$, $12^{th}$, $15^{th}$, and $18^{th}$ month of supplementation.

The following biochemical and immunological parameters were investigated on each visit for comparison with pre-treatment data and between group data:

Stimulated and unstimulated ex vivo peripheral blood mononuclear cell cytokine production: changes in TGF-β1, IFN-γ, TNF-α, IL-1β, IL-6 and IFN-β, which are implicated in the pathogenesis of MS. Cytokine and related gene expression.

Soluble adhesion molecules in serum particularly ICAM-1 and VCAM-1

Peripheral blood mononuclear cell membrane fatty acids and plasma phospholipid fatty acid composition.

Results are shown in Tables 1 and 2 and FIGS. 1 to 5.

The primary outcome parameter was the number of clinical relapses between baseline (Month 0) and the end of treatment (Month 18). Secondary outcome parameters included: the time to first clinical relapse; severity of relapses, as assessed by EDSS score and the use of steroid treatment; and changes in EDSS at Month 3, 6, 9, 12, and 18 compared to baseline and defined as at least 1.0 point increase in the EDSS that is sustained for 3 months or at least 1.5 point increase on the EDSS from the baseline EDSS that is sustained for 3 months.

Eleven patients were in the placebo group, seven patients had been taking low-dose Borage oil, and ten patients had been taking high-dose Borage oil. The study drug was well-tolerated, and there were no serious adverse events during the 18-month trial.

Isolation and Culture of PBMC

Heparinised whole blood was diluted with an equal volume of Hanks' balanced salt solution (Sigma, UK) and the resulting diluted blood layered onto Lymphoprep (Nycomed, Oslo, Norway). Following density centrifugation at 800 g for 30 minutes the PBMC were removed from the interface and diluted in Hanks' solution. The cells were then washed twice by centrifugation for 10 minutes at 250 g. The resulting final pellet was then resuspended in culture medium consisting of RPMI-1640 medium (Sigma, UK) supplemented with 2 mM L-glutamine, 100 U penicillin and 100 μg streptomycin (Sigma, UK) and 10% autologous plasma. $2 \times 10^6$ per ml PBMC, >95% viable as judged by trypan blue exclusion, were added to tissue culture tubes (Bibby Sterilin Ltd, Stone, UK) and incubated for 24 h at 37° C. with 5% $CO_2$. The concentration of antigen, cell density and time of culture were all determined in previous kinetic experiments to determine maximum cytokine production (data not shown). Routine cytospin preparations were also prepared for subsequent differential counts. Following incubation the cells were removed from culture by centrifugation at 250 g for 10 minutes, the resulting supernatants were then removed, aliquoted and stored at −70° C.

Preparation of Plasma Samples 10 ml of heparinised blood was spun at 250 g for 10 minutes. The resulting plasma layer was then removed, aliquoted and stored at −70° C.

Detection of Pro-inflammatory Cytokines

TNF-α, IL-1β and IFN-γ in cell culture supernatants and plasma were detected using commercially available paired antibodies enabling cytokine detection in an ELISA format (R&D systems Ltd, Abingdon, UK). The sensitivities for the TNF-α and IFN-γ ELISAs were 15.6-1000 pg/ml and 3.9-250 pg/ml for IL-1β.

Detection of Biologically Active TGF-β1

Biologically active TGF-β1 in cell culture supernatants and plasma were detected using the commercially available $E_{max}$ ELISA system with a sensitivity of 15.6-1000 pg/ml (Promega, Southampton, UK).

Statistical Analysis

Differences in cytokine production were compared using Student's t-test and Mann-Whitney U-test and were considered significant when p values were less than 0.05.

RESULTS

Two patients had developed diarrhoea, both of whom were later confirmed to have been taking high-dose Borage oil. The diarrhoea was mild in one patient, but was moderately severe in the second patient, who later discontinued the study drug. The code was not broken and the diarrhoea had stopped after the discontinuation of the drug, but reappeared upon re-challenge. Therefore, this patient was withdrawn from the trial. The remaining patients who were treated with high-dose Borage oil showed excellent clinical improvement on all primary and secondary outcome criteria. For example, their mean EDSS score after 6 months of treatment had improved from baseline EDSS (FIG. 1). More importantly, the mean number of clinical relapses had significantly reduced after 6 months of treatment when compared to the number of relapses in the placebo group (FIG. 2). In contrast, patients who had been receiving low-dose Borage oil did not show any clinical improvement when compared to the placebo group. In addition to its beneficial effect on MS disease activity, high dose Borage oil provided some symptomatic relief of muscle spasticity (stiffness) and painful sensory symptoms, and also improved cognitive functions.

As can be seen for the figures below, relapse rate after 9, 12 and 18 months was down to zero in the high dose group. The increase seen at 15 months was due to the patient dropping out of this group.

The following are three brief case histories to illustrate the therapeutic benefits of high dose high sn-2 GLA Borage oil. The first two are from the trial while the third is a post trial patient for whom MRI studies were obtained.

Patient 1 (Treatment):

The first patient was a 48 year old woman who had had a clinically active, relapsing remitting MS for 9 years. She had originally worked as a full-time administrator at the local Health Authority, but she was unable to perform her duties because of her severe MS. Therefore, she later worked as a part-time secretary, but still had difficulties in mobilization because of muscles stiffness and sensory disturbances. She was also experiencing severe clinical relapses at an average of one relapse every nine months. Most of these relapses had resulted in hospital admissions for steroid therapy. In view of her active MS, she was recruited into the Borage oil trial. There were no adverse events relating to the study, and after taking the medication for four months, she experienced good improvement in her walking and sensory symptoms.

About nine months after therapy, she was well enough to start full-time employment. In addition, she remained relapse-free for the 18-month duration of the clinical trial. Following the conclusion of the trial, the treatment code revealed that she was taking high-dose Borage oil.

Patient 2 (Control):

The second case was a 46-year old woman who also had a clinically active relapsing remitting MS for 8 years. She had originally worked as a shop assistant, but became unemployed after MS was diagnosed.

Her symptoms included difficulty with mobilisation and painful sensory symptoms in both legs. She had experienced three clinical relapses in the two years preceding the clinical trial, and had been admitted to hospital twice for steroid therapy. Consequently, she was recruited into the Borage oil trial, but her walking continued to deteriorate. Six months into the trial, she need to use a walking stick and also received treatment with Baclofen to reduce low limb spasticity. Approximately ten months after starting the Borage oil trial, she was admitted to hospital because of severe clinical relapse, which was treated with steroids. She later developed bladder disturbances and began to use a wheelchair for long journeys. The treatment code was broken after the conclusion of the 18-month trial, and she was found to have been taking placebo. Since then, she started using a walking frame for journeys exceeding 50 yards.

Patient 3: Treatment (Additional to Trial)

The third case was a 26 year-old man who was diagnosed with definite MS in April 2001. His symptoms had started in 1999 when he complained of diffuse, intractable pain affecting various parts of his body, particularly the left side of the chest and abdomen. This was followed by intermittent numbness in the hands and feet, associated with fluctuating weakness. There were also distressing bladder symptoms in the form of urinary frequency and urgency. The diagnosis of MS in 2001 was based on his relapsing remitting symptoms, and was confirmed by positive cerebrospinal fluid analysis and magnetic resonance imaging (MRI) of the brain, which showed multiple white matter abnormalities in both cerebral hemispheres. Symptoms did not respond to various pharmaceutical therapies.

In April 2003, oral supplementation with the present high dose Borage oil was commenced. The patient reported dramatic improvement in his symptoms within three months of starting this oral supplementation. His painful sensory symptoms disappeared completely. He reported no numbness or weakness since May 2003, and noticed significant improvement in his bladder control. The oral supplementation caused no adverse events. A repeat brain MRI was undertaken to verify the reported improvement in Mr N's symptoms. The repeat MRI showed a reduction in the size and distribution of the white matter abnormalities.

Examples

Structured sn-2 Lipids

In all the examples below higher purity is obtained by use of higher purity starting material γ-linolenic, dihomo-γ-linolenic or arachidonic acid, such as is available eg from Sigma Aldrich. GLA 95 indicates 95% pure γ-linolenic acid.

Synthesis Example 1

Synthesis of Trigammalinolenin

1) Acid Chloride Method 2.0 g (7.2 mmol, 3.1 equiv) GLA95 (95% pure γ-linolenic acid) was dissolved in 10 ml DCM. 1.01 g (0.71 ml, 8.0 mmol, 3.4 equiv) oxalyl chloride in 5 ml DCM added dropwise over 2-3 min under nitrogen. Stirred at RT overnight. Reaction mixture concentrated in vacuo to remove DCM and excess oxalyl chloride. This acid chloride was then added dropwise over 2-3 min to a stirred mixture of 215 mg (2.3 mmol, 1 equiv) of glycerol, 0.58 ml (3.1 equiv) pyridine and 10 ml DCM under nitrogen. The mixture was stirred at RT overnight. The pyridine hydrochloride formed was then filtered off and washed with DCM. The solution was washed 1×4 ml water, 0.1N HCl, 5% sodium bicarbonate and 5% NaCl. Dried over magnesium sulphate, filtered and concentrated in vacuo to a yellow oil. This oil was purified on a silica column using 10% ether in hexane as eluting solvent. A clear colourless oil was obtained, a sample of which was trans-esterified and subsequently analysed by GC. The product contained 96.3% GLA 2) DCCl Method 2.19 g GLA95 (3.15 equiv), 230 mg (1 equiv) glycerol, 153 mg DMAP (0.5 equiv) were stirred in 10 ml DCM under nitrogen. 1.85 g DCCl (3.6 equiv) in 5 ml DCM was added. The reaction mixture was stirred at RT under nitrogen overnight. The DCU formed was filtered and washed with DCM. DCM washed 1×5 mls N HCl, water, 5% sodium bicarbonate and water. Dried over magnesium sulphate, filtered and concentrated in vacuo to an oil. This oil was then purified on a silica column using 10% ether in hexane as eluting solvent. 1.47 g (67%) of a slightly cloudy oil was obtained. A sample of this product was trans-esterified and subjected to GC analysis. The product contained 95.8% GLA.

Scale-up 20 g (0.072 mol, 3.1 equiv) of GLA95 (gamma linolenic acid, 95%) was dissolved in 100 ml DCM. 13.7 g (9.3 ml, 0.11 mol, 4.78 equiv) oxalyl chloride was added over 3-4 min under nitrogen. The reaction mixture was stirred under nitrogen overnight. It was then concentrated in vacuo to remove DCM and excess oxalyl chloride. This oil was then added dropwise over ca 5 min to a stirred mixture of 2.14 g (0.023 mol, 1 equiv) of glycerol, 100 ml DCM and 5.8 ml (5.68 g, 0.072 mol, 3.1 equiv) of pyridine under nitrogen. 85 mg (0.7 mmol, 0.03 equiv) of DMAP (4-dimethylaminopyridine) catalyst was added. The mixture was stirred at RT overnight. Pyridine hydrochloride was filtered off and washed with DCM. The DCM solution was washed 1×25 ml: water, 10% sodium bicarbonate, 0.1N HCl, 5% NaCl. (Emulsions formed during this process, especially at first). The DCM was dried over magnesium sulphate, filtered and concentrated in vacuo to a brown oil (~21 g).

The oil was purified on a silica column using 5% ether in hexane at first and then 10%. 15.6 g (77% yield) of a clear oil was obtained. By tlc this material contained a small amount of free GLA. (This material was repurified at a later date)

Large Scale-up

The above reaction was repeated on 10 times scale. Thus, 200 g of GLA95, 1 L DCM, 137 g of oxalyl chloride, and 21.4 g of glycerol were used. On the addition of the acid chloride the reaction mixture was cooled in a cold water bath and the temperature kept below 35° C. 250 g of a brown oil were produced. This was initially purified on a 500 gram silica column. The oil was dissolved in 200 ml hexane and applied to the column. The column was eluted at first with hexane, then 5% ether in hexane and then 10%. Fractions were collected and analysed by tlc eventually yielding two batches of oils. The first A (66 g) contained a small amount of front running impurity and a little GLA (slower running than TGL), the second fraction B (99 g) was clear of front running impurity and contained a little GLA.

The large scale reaction was repeated using 169 g of GLA and gave two fractions as above. This time there was 85 g of 'A' fraction and 54 g of 'B' fraction. Both batches of 'A' were combined and re-purified on a 500 g silica column. The 'B' fractions were treated in a similar manner (15 g of material from the small-scale reaction were also added to this batch).

Some fractions from the above were again re-purified to eventually give 259 grams of oil. The oil was pumped down on a rotary evaporator under high vacuum to constant weight—256 g. This represents an overall yield of 65%.

Analysis of Product
GC
A small sample was trans-esterified and subjected to GC analysis:

The GLA content was 97.1%. The main impurity was linoleic acid –1.91%.

Note: The original GLA95 that was used for the synthesis contained 96.2% GLA and 2.42% linoleic acid.

HPLC

An HPLC method was developed using a reversed phase column (Hypersil C18 4.6×100 mm), eluting with 80/20 acetonitrile/THF. Detection was by UV at 210 nm. This showed the product to be a mixture of three components. The main peak (93.6%) was the required product. A slower running impurity (representing 5.0% of the product) was probably a GGLl triglyceride (L1=linoleic acid). A second impurity was slightly faster running and represented 1.4% of the product.

Note: Absorption at 210 nm varies considerably between triglycerides of differing fatty acid content. For example trigammalinolenin has a UV absorbtion 5-6 times greater than that of trilinolenin Summary 254 g of glycerol tri-6,9,12-linolenate (gamma linolenic acid triglyceride, trigammalinolenin, GGG) was prepared from 96.2% GLA by a two-step acid chloride route. It is a clear, pale yellow oil and was stored under nitrogen in the freezer. The GLA content was 97.1% and no C20:1, C22:1, or C24:1 acids were detected). The HPLC purity was 93.6%. Synthesis of higher purity GGG would is readily achievable using GLA 98 (98% γ-linolenic acid: Scotia) or higher starting material.

Comparative Lipid 1

Synthesis Tricaprin (Glycerol tridecanoate)

Small Scale

Glycerol (3.0 g, 0.0325 mol, 1 eq) pyridine (8.1 ml, 0.10 mol, 3.1 eq) and dichloromethane (100 ml) were stirred at room temperature under nitrogen. Decanoyl chloride (21 ml, 19.25 g, 0.10 mol, 3.1 equiv) was then added dropwise over 5 min, with external cooling in a water bath to keep the temperature at 30-35° C. When the addition was complete 4-dimethylaminopyridine (DMAP (0.12 g, 1 mmol, 0.03 eq) was added and the mixture stirred under nitrogen at room temperature overnight. The precipitated pyridine hydrochloride was removed by filtration and washed with dichloromethane. The combined washing and filtrate was then washed with aqueous solutions (20 ml) of 5% sodium chloride, 5% sodium bicarbonate, 0.1N hydrochloric acid, and 5% sodium chloride. The dichloromethane layer was then dried over $MgSO_4$ and the solvent removed in vacuo. The residual oil crystallised on standing. This material was recrystallised from isopropanol (40 ml) to give 15.6 g (86% yield) of a waxy white solid.

Analysis
GC—99.8% pure
HPLC
(C18 4.6×100 mm, ACN/THF 85/15 1 ml/min, λ 210 nm)—94.9% pure Large Scale The above was repeated on 15 times the scale. Glycerol (45.0 g, 0.49 mol, 1 eq), pyridine (121.5 ml, 1.50 mol, 3.1 eq) and dichloromethane (1.5 L) were stirred at room temperature under nitrogen. Decanoyl chloride (315 ml, 288.8 g, 1.50 mol, 3.1 equiv) was then added dropwise over 15 min, with external cooling in a water bath to keep the temperature at 30-35° C. When the addition was complete 4-dimethylaminopyridine (DMAP (1.8 g, 15 mmol, 0.03 eq) was added and the mixture stirred under nitrogen at room temperature overnight. The precipitated pyridine hydrochloride was removed by filtration and washed with dichloromethane. The combined washing and filtrate was then washed with aqueous solutions (300 ml) of 5% sodium chloride, 5% sodium bicarbonate, 0.1N hydrochloric acid, and 5% sodium chloride. The dichloromethane layer was then dried over $MgSO_4$ and the solvent removed in vacuo. The residual oil crystallised on standing. This material was recrystallised from isopropanol (400 ml) to give 228 g (86% yield) of a waxy white solid.

Analysis
GC—99.8% pure
HPLC
(C18 4.6×100 mm, ACN/THF 85/15 1 ml/min, λ 210 nm)—94.9% pure A further batch was made and combined with the small-scale batch above and recrystallised from isopropanol to give 44 g of product. The above batches were combined (268 g) and reanalysed:

GC
99.9% pure
HPLC
97.9%

Summary 263 g of glycerol tridecanoate (tricaprin, CCC) was been prepared from decanoyl chloride (98%) by a one-step process (scheme given below). It is a white, low-melting solid and was stored under nitrogen in the freezer. The C content was 99.9% of fatty acid content and the HPLC purity was 97.9%.

Synthesis Example 2

1,3-Dicaprin 2-gammalinolenoate (Glycerol 1,3-didecanoate 2-octadecatri(6-Z9-Z,12-Z)enoate or CGC)

This triglyceride is novel. Unlike CGC, its isomer CLnC (Ln=α-linolenic acid), has been identified (see K. Long et al *Biotechnol. Lett.*, 20, 369-372 (1998). and H. Mu, P. Kalo et al, *Eur. J. Lipid Sci. Technol.*, 102, 202-211 (2000). as a component of coconut oil. In addition, CLxC (Lx=a linolenic acid of unspecified double bond position) has been described (see J. Gresti et al. *J Dairy Sci.*, 76, 1850-1869 (1993)), The two intermediates used in the synthesis of CGC are known (see L. El Kihel et al *Arzneim-Forsch./Drug Res.*, 46, 1040-1044 (1996) and U.S. Pat. No. 4,178,299. The last step described below is novel and the first two stages are also inventive since they are more suitable for large scale production than those previously reported.

CGC was prepared by reaction of 1,3-Dicaprin with GLA-chloride in dichloromethane-pyridine. 1,3-Dicaprin was prepared by sodium borohydride reduction of 1,3-didecanoyloxypropan-2-one, which was in turn prepared by reaction of decanoyl chloride with 1,3-dihydroxyacetone. The intermediate 1,3-dicaprin must be handled with care since it can undergo acyl migration on exposure to acids, bases and heat. An older method of making 1,3-dicaprin has been described (see A. P. J. Mank et al *Chem. Physics Lipids*, 16, 107-114 (1976).

A versatile, flexible synthesis of 1,3-diglycerides and triglycerides. by catalysed addition of decanoic acid to a glycidol ester (from epichlorohydrin) is less attractive because of more severe reaction conditions and acyl migration problems. The final product, CGC, was purified by careful column chromatography on silica which removed by-products.

Small Scale

1,3-didecanoyloxypropan-2-one

Decanoyl chloride (40.0 ml, 36.8 g, 0.19 mol, 1.98 equiv) was added dropwise over 10-15 min to a stirred suspension of 1,3-dihydroxyacetone dimer (8.68 g, 0.048 mol, 1.0 equiv), pyridine (15.6 ml, 0.19 mol), 4-dimethylaminopyridine (0.18 g, 0.0014 mol, 0.03 equiv) and dichloromethane (DCM, 150 ml) at room temperature under nitrogen. The temperature of the reaction mixture was kept below 30° C. by cooling in a cold water bath. The reaction mixture was stirred at RT under nitrogen overnight. The pyridine hydrochloride formed was removed by filtration and washed with DCM. The combined filtrate and washings were then washed with 1×25 ml portions of 5% NaCl, 5% NaHCO$_3$, 0.1N HCl, 5% NaCl. The solution was then dried over MgSO$_4$ and concentrated in vacuo to a yellowish semi-solid. This was then crystallised from methanol (150 ml) to give a white solid. The yield was 28.2 g (73%).

1,3-Dicaprin

The above ketone (28.2 g, 0.071 mol) was dissolved in tetrahydrofuran (THF, 200 ml). Water (10 ml) was then added, the solution cooled to 5° C., and sodium borohydride (5.38 g, 0.14 mol) added portionwise below 10° C. The reaction mixture was stirred at RT for 1 h and then concentrated in vacuo to remove THP. The residue was partitioned between ethyl acetate and 5% sodium chloride solution. The aqueous phase was re-extracted with ethyl acetate and the combined extracts dried over MgSO$_4$ and concentrated in vacuo to a waxy solid. This was crystallised twice from hexane to give 11.2 g (40%) of a white solid. (99%+pure by HPLC)

1,3-Dicaprin 2-gammalinolenoate (CGC)

Gamma-linolenic acid (GLA95, 8.34 g, 0.03 mol) was dissolved in dichloromethane (DCM, 60 ml). The resulting solution was stirred at RT under nitrogen and oxalyl chloride (3.9 ml, 5.67 g, 0.044 mol) added dropwise over 5 mins. The mixture was stirred at RT overnight and then concentrated in vacuo to remove DCM and excess oxalyl chloride. The residual oily acid chloride (GLA-Cl) was then added dropwise over 15 min (ice/water cooling) to a stirred solution of 1,3-dicaprin (11.2 g, 0.028 mol), DCM (50 ml), pyridine (2.42 ml, 2.37 g, 0.03 mol) and 4-dimethylaminopyridine (0.10 g, 0.0008 mol, 0.03 equiv) at 10-15° C. The temperature was maintained by ice-water cooling. The reaction mixture was stirred at RT under nitrogen overnight. Pyridine hydrochloride was removed by filtration and washed with DCM. The combined washing and filtrate was washed with 1×20 ml portions of 5% NaCl, 5% NaHCO$_3$, 0.1N HCl, 5% NaCl. The solution was then dried over MgSO$_4$ and the solvent removed in vacuo. The residual brown oil was purified by column chromatography on silica. Elution with hexane and then with 5% ether/hexane gave 10.3 g (56%) of a colourless oil. The structure was confirmed by $^{13}$C NMR and GLC. Purity determined by HPLC.

Large Scale

1,3-didecanoyloxypropan-2-one

Decanoyl chloride (272 ml, 250 g, 1.3 mol, 2 equiv) was added dropwise over 10-15 min to a stirred suspension of 1,3-dihydroxyacetone dimer (59.1 g, 0.65 mol, 1.0 equiv), pyridine (106 ml, 103.7 g 1.3 mol), 4-dimethylaminopyridine (2.38 g, 0.02 mol, 0.03 equiv) and dichloromethane DCM, 750 ml) at room temperature under nitrogen. The temperature of the reaction mixture was kept below 30° C. by cooling in a cold water bath. The reaction mixture was stirred at RT under nitrogen overnight. The pyridine hydrochloride formed was removed by filtration and washed with DCM. The combined filtrate and washings were then washed with 1×150 ml portions of 5% NaCl, 5% NaHCO$_3$, 0.1N HCl, 5% NaCl. The solution was then dried over MgSO$_4$ and concentrated in vacuo to a yellowish semi-solid. This was then crystallised from methanol (500 ml) to give a white solid. The yield was 158 g (60%).

1,3-Dicaprin

The above ketone (158 g, 0.40 mol) was dissolved in tetrahydrofuran (THF, 2.25 L). Water (50 ml) was then added, the solution cooled to 5° C., and sodium borohydride (5.66 g, 1.5 eq) added portionwise below 10° C. The reaction mixture was monitored by HPLC (C18, eluted with ACN at 1 ml/min λ210 nm) (Note: only about 4.5 g of the borohydride was in fact added, as all SM had reacted). The reaction mixture was stirred at RT for 1 h and then concentrated in vacuo to remove THF. The residue was partitioned between ethyl acetate and 5% sodium chloride solution. The aqueous phase was re-extracted with ethyl acetate and the combined extracts dried over MgSO$_4$ and concentrated in vacuo to a waxy solid. This was crystallised twice from hexane to give 96 g (60%) of a white solid. (98% pure by HPLC)

1,3-Dicaprin 2-gammalinolenoate (CGC)

Gamma-linolenic acid (GLA95, 120.2 g, 0.43 mol) was dissolved in dichloromethane (DCM, 750 ml). The resulting solution was stirred at RT under nitrogen and oxalyl chloride (55.7 ml, 82.3 g, 0.65 mol, 1.5 eq) added dropwise at 15-20° C. over 15 mins. The mixture was stirred at RT overnight and then concentrated in vacuo to remove DCM and excess oxalyl chloride. The residual oily acid chloride (GLA-Cl) was then added dropwise over 30-40 min at 10-15° C. (ice/water cooling) to a stirred solution of 1,3-dicaprin (164.7 g, 0.41 mol), DCM (650 ml), pyridine (33.3 ml, 32.5 g, 0.41 mol) and 4-dimethylaminopyridine (1.50 g, 0.012 mol, 0.03 equiv) at 10-15° C. The reaction mixture was stirred at RT under nitrogen overnight. Pyridine hydrochloride was removed by filtration and washed with DCM. The combined washing and filtrate was washed with 1×150 ml portions of 50% NaCl, 5% NaHCO$_3$, 0.1N HCl, 5% NaCl. The solution was then dried over MgSO$_4$ and the solvent removed in vacuo to a brown oil (275 g).

The scale of the above three reactions was the largest on which each was carried out. The borohydride reduction produced, in addition to 1,3-dicaprin, a by-product in variable yield. The presence of this by-product greatly affected the yield of the isolated pure 1,3-dicaprin; the by-product could only be removed by two crystallisations of the crude product. Since the final product, CGC, is purified by column chromatography, it is imperative that the 1,3-dicaprin used for the final step is as pure as possible!

From the above reactions about 440 g of crude CGC was produced as a brown oil. This was purified on a series of silica columns using hexane followed by 2-3% ether/hexane. The purification required 7 or 8 columns, using 3-4 kilos of silica, 25-30 liters of solvent (recycling solvent kept this figure low—in practice over 100 liters were used)

The resulting product, a clear almost colourless oil, (264 grams) was 96.4% pure by HPLC (C18 4.6×100 mm, eluted with 85/15 ACN/THF at 1 ml/min. UV detection λ210 nm). GC indicated a ratio of 66.1/33.9 C/G. NMR analysis indicated the product to have the correct CGC structure and be of at least 95% purity: $\delta_C$ (500 MHz, CDCl$_3$) 172.65 (2-GLA carbonyl), 173.25 (1,3-capric carbonyl). Ratio of signals 2.04:1. No signal at 173.0 indicating absence of 1,3-GLA. Trace signal at 172.79 could be oleic acid impurity in GLA or 2-capric acid.

Summary 264 g of glycerol 1,3-didecanoate-2-gammalinolenoate (1,3-dicaprin-2-GLA, CGC) has been prepared from decanoyl chloride (98%) by a three-step process (scheme given below). It is an almost colourless oil (slight yellow tinge) and was stored under nitrogen in the freezer. The HPLC purity was 96.4%.

Synthesis Example 3

1,3-Didecanoate-2-dihomo-γ-liunolenoate (Glycerol 1,3-didecanoate2-eicosa-(8Z,11Z,14Z)-trienoate or C(DHLA)C This triglyceride appears to be novel—no reference to it has been found.

DHLA (3.93 g, 12.8 mmol, 1 eq) was dissolved in dichloromethane (DCM, 20 ml) and stirred at room temperature under a nitrogen atmosphere. Oxalyl chloride (1.69 ml, 2.46 g, 19.4 mmol, 1.5 eq) was added dropwise over 1-2 min, and left stirring at room temperature overnight. The resulting solution was concentrated in vacuo to remove DCM and excess oxalyl chloride. The residual oily acid chloride (DHLA-Cl) was then added dropwise over 5 min at 25° C. to a stirred mixture of 1,3-dicaprin (4.91 g, 12.2 mmol, 0.95 eq), pyridine (0.98 ml, 0.96 g 12.1 mmol, 0.95 eq) and 4-dimethylam inopyridine (DMAP, 8 mg, 0.07 mmol, 0.03 eq). The reaction temperature rose to 32° C. during the addition. The reaction was stirred at 30-35° C. and monitored by HPLC. The reaction was stopped after 1.5 h. The precipitated pyridine hydrochloride was filtered off and washed with DCM. The combined filtrate and washings were then washed with 1×10 ml portions of 5% NaCl, 5% NaHCO$_3$, 0.1N HCl, 5% NaCl. The solution was then dried over MgSO$_4$ and concentrated in vacuo to give the crude product as a yellow-orange oil (8.9 g, 86% purity by HPLC). This oil was chromatographed on silica gel (250 g). Elution with hexane and diethyl ether-hexane (2-6%) gave a purified product as a pale yellow oil. Treatment of a hexane solution with decolourising charcoal and removal of the solvent in vacuo gave C(DHLA)C as a clear colourless oil (6.48 g, 98.9% purity by HPLC).

Synthesis Example 4

Triarachidin (Glycerol trieicosotetra5-Z,8-Z,11-Z,14Z-eneoate) or AAA

Arachidonic acid (50.9 g, 0.17 mol, 3 eq) was dissolved in dichloromethane (DCM, 175 ml) and stirred at room temperature under a nitrogen atmosphere. Oxalyl Chloride (21.9 ml, 31.9 g, 0.25 mol, 4.4 eq) was then added to the stirred solution over 5 min and the temperature increased by 4° C. The resulting yellow-green mixture was stirred at RT overnight and then concentrated in vacuo to remove DCM and excess oxalyl chloride. The residual oily acid chloride (A-Cl) was then added dropwise over 15 min to a pre-warmed (25° C.) stirred mixture of glycerol (5.11 g, 0.055 mol, 1 eq), pyridine (13.5 ml, 13.2 g, 0.17 mol, 3 eq) and 4-dimethylamino pyridine (DMAP, 0.20 g, 0.002 mol, 0.03 eq). The temperature of the reaction mixture rose to 42° C. during the addition and a gentle reflux was observed. The mixture was stirred at 30-40° C. and monitored by HPLC. After 2 h, no further product formation was observed. The precipitated pyridine hydrochloride was filtered off and washed with DCM. The combined filtrate and washings were then washed with 1×50 ml portions of 5% NaCl, 5% NaHCO$_3$, 0.1N HCl, 5% NaCl. The solution was then dried over MgSO$_4$ and concentrated in vacuo to give the crude product as a yellow-orange oil (57 g). This oil was purified by column chromatography on silica gel (ca. 600 g). Elution with hexane and diethyl ether(2-4%)-hexane gave 22.8 g of the product as an oil. A second batch (17.8 g) was produced from 39.8 g of arachidonic acid, The two batches were combined and residual solvents removed under vacuo to give 40.5 g (43%) of a mobile pale yellow oil. HPLC purity 84.8% GLC analysis 94.3% AA (arachidonic acid).

Comparative Lipid 2

1,3-Di(octadeca-6Z,9Z,12Z-enoyloxy)propan-2-one (1,3-Di(γ-linolenoyloxy)propan-2one, GonG) Stage 1 Intermediate for GCG Gamma-linolenic acid (GLA95, 197 g, 0.71 mol, 2.2 equiv) was dissolved in dichloromethane (DCM, 600 ml) contained in a 2 L 3 necked flask. The resulting solution was stirred at RT under nitrogen. Oxalyl chloride (93 ml, 136 g, 1.07 mol, 3.3 eq) was added dropwise at 15-20° C. over 15 min. The brown mixture was stirred at RT overnight and then concentrated in vacuo to remove DCM and excess oxalyl chloride. The residual oily acid chloride (GLA-Cl) was then added dropwise over 20 min at 25° C. to a stirred mixture of 1,3-dihydroxyacetone dimer (28.99 g, 0.32 mol, 1.0 equiv), pyridine (52 ml, 50.9 g 0.64 mol, 2.0 equiv), 4-dimethylaminopyridine (2.36 g, 0.02 mol, 0.06 equiv) and dichloromethane (DCM, 600 ml) at room temperature under nitrogen. The temperature of the reaction mixture was allowed to rise to 40° C. and the mixture was stirred for a further 2 h under nitrogen (monitored by HPLC). The pyridine hydrochloride that formed was removed by filtration and washed with DCM. The combined filtrate and washings were then washed with 1×150 ml portions of 5% NaCl, 5% NaHCO$_3$, 0.1N HCl, 5% NaCl. The solution was then dried over MgSO$_4$ and concentrated in vacuo to give ca. 200 g of a yellow oil. This material was partially purified by column chromatography on silica (600 g). Elution with hexane and then ether-hexane mixtures (2-15%) gave 42 g of a pale yellow oil. This oil was chromatographed again on silica (600 g) and eluted with hexane and then 1-10% ether-hexane to give the product (95.9% purity) as a pale yellow oil. The yield was 42 g (17%).

1,3-Di(octadeca-6Z,9Z,12Z-enoyloxy)propan-2-ol (1,3-Di(γ-linolenoyloxy)propan-2-ol or 1,3-Di-gamma-linolenin GolG) Stage 2 Intermediate for GCG 13-Di(γ-linolenoyloxy)propan-2-one (GonG, 25.5 g, 0.04 mol, 1 eq) was dissolved in tetrahydrofuran (THF, 375 ml) and water (12.7 ml). The solution was vigorously stirred at −20° C., care was taken to keep the reaction temperature below −15° C. Sodium borohydride (790 mg, 0.02 mol, 1.25 eq) was added portionwise to the stirred solution over 3 mins.

The reaction mixture was stirred for a further 10 mins at −20° C. and hexane (380 ml) then added. The still cold mixture was then washed with water (2×200 ml), dried over MgSO$_4$ and concentrated in vacuo to give the title compound as a brown oil (27.8 g) (82.6% purity by HPLC, less than 1% migrated material). Another batch was prepared and combined with the first to give 50 g of crude product. This material was purified by column chromatography on silica gel (400 g). Elution with hexane and diethyl ether-hexane mixture (5-20%) gave 36.1 g of the product as a pale oil (91.5% purity).

(N.B. Care should be taken not to leave the compound on the silica overnight as it appears to undergo a migration reaction, giving GGol)

1,3-Di-γ-linolenin 2-decanoate (Glycerol 1,3-dioctadeca-(6Z,9Z,12Z)-trienoate 2-decanoate or GCG)

Decanoyl chloride (13.5 ml, 12.4 g, 0.065 mol, 1.1 eq) was added to a stirred solution of 1,3-di-γ-linolenin (36.1 g, 0.059 mol, 1 eq), dry pyridine (5.7 ml, 5.6 g, 0.07 mol, 1.1 eq), 4-dimethylaminopyridine (0.2 g, 0.002 mol, 0.03 eq) and dichloromethane (DCM, 150 ml) over ca. 10 mins. The temperature was maintained at 17° C.-23° C. during addition. The reaction was then stirred at 30-35° C. and monitored by HPLC. A further 1-2 ml of decanoyl chloride was added after 1 h, 1.5 h and 2 h. Further addition appeared to increase the conversion to product as determined by HPLC. After 3 h the reaction mixture was filtered and the filtrate washed with DCM. The combined filtrate and washings were then washed with 1×50 ml portions of 5% NaCl, 5% NaHCO$_3$, 0.1N HCl, 5% NaCl. The DCM extract was then dried over MgSO$_4$ and concentrated in vacuo to give the crude product as a pale yellow oil; (purity 90% by HPLC). The oil was purified by column chromatography on silica gel (600 g). Elution with hexane and diethyl ether-hexane (1.5-2.5 then 3.5%) gave the product (GCG.) as a clear oil; (35.5 g 96.1% purity by HPLC). Another 7.5 g of pure lipid was obtained by further chromatography on some of the fractions containing only a small amount of impurity.

Synthesis Example 5

1,3-Dicaprin 2-arachidonate (Glycerol 1,3-didecanoate 2-eicosatetra-(5-Z,8-Z,11-Z,14-Z)enoate or CAC)

This triglyceride is known. CAC has been identified as a constituent of lymph lipids following administration of safflower oil to rats. WO 03 013,497 describing an arachidonic acid containing triglyceride (produced by culturing *Mortierella alpina*) useful for diseases caused by brain hypofunction, but specifically for cognition enhancement. The two intermediates used in the synthesis of CAC are known.

The synthesis of CAC from 1,3-dicaprin, and the purification of this are all novel.

Here CAC was prepared by reaction of 1,3-Dicaprin with arachidonyl chloride in dichloromethane-pyridine. 1,3-Dicaprin was prepared by sodium borohydride reduction of 1,3-didecanoyloxypropan-2-one, which was in turn prepared by reaction of decanoyl chloride with 1,3-dihydroxyacetone. The intermediate 1,3-dicaprin must be handled with care since it can undergo acyl migration on exposure to acids, bases and heat. An older method[6] of making 1,3-dicaprin, by catalysed addition of decanoic acid to a glycidol ester (from epichlorohydrin) was deemed less attractive because of more severe reaction conditions and acyl migration problems. The final product, CAC, was purified by careful column chromatography on silica which removed by-products.

1,3-Dicaprin 2-arachidonate (CAC)

Arachidonic acid (AA96, 8.34 g, 0.03 mol) was dissolved in dichloromethane (DCM, 60 ml). The resulting solution was stirred at RT under nitrogen and oxalyl chloride (3.9 ml, 5.67 g, 0.044 mol) added dropwise over 5 mins. The mixture was stirred at RT overnight and then concentrated in vacuo to remove DCM and excess oxalyl chloride. The residual oily acid chloride (GLA-Cl) was then added dropwise over 15 min (ice/water cooling) to a stirred solution of 1,3-dicaprin (11.2 g, 0.028 mol), DCM (50 ml), pyridine (2.42 ml, 2.37 g, 0.03 mol) and 4-dimethylaminopyridine (0.10 g, 0.0008 mol, 0.03 equiv) at 10-15° C. The temperature was maintained by ice-water cooling. The reaction mixture was stirred at RT under nitrogen overnight. Pyridine hydrochloride was removed by filtration and washed with DCM. The combined washing and filtrate was washed with 1×20 ml portions of 5% NaCl, 5% NaHCO$_3$, 0.1N HCl, 5% NaCl. The solution was then dried over MgSO$_4$ and the solvent removed in vacuo. The residual brown oil was purified by column chromatography on silica. Elution with hexane and then with 5% ether/hexane gave 10.3 g (56%) of a colourless oil. The structure was confirmed by $^{13}$C NMR and GLC. Purity determined by HPLC.

Large Scale

1,3-didecanoyloxypropan-2-one

Decanoyl chloride (272 ml, 250 g, 1.3 mol, 2 equiv) was added dropwise over 10-15 min to a stirred suspension of 1,3-dihydroxyacetone dimer (59.1 g, 0.65 mol, 1.0 equiv), pyridine (106 ml, 103.7 g 1.3 mol), 4-dimethylaminopyridine (2.38 g, 0.02 mol, 0.03 equiv) and dichloromethane (DCM, 750 ml) at room temperature under nitrogen. The temperature of the reaction mixture was kept below 30° C. by cooling in a cold water bath. The reaction mixture was stirred at RT under nitrogen overnight. The pyridine hydrochloride formed was removed by filtration and washed with DCM. The combined filtrate and washings were then washed with 1×150 ml portions of 5% NaCl, 5% NaHCO$_3$, 0.1N HCl, 5% NaCl. The solution was then dried over MgSO$_4$ and concentrated in vacuo to a yellowish semi-solid. This was then crystallised from methanol (500 ml) to give a white solid. The yield was 158 g (60%).

1,3-Dicaprin

The above ketone (158 g, 0.40 mol) was dissolved in tetrahydrofuran (THF, 2.25 L). Water (50 ml) was then added, the solution cooled to 5° C., and sodium borohydride (5.66 g, 1.5 eq) added portionwise below 10° C. The reaction mixture was monitored by HPLC (C18, eluted with ACN at 1 ml/min λ210 nm) (Note: only about 4.5 g of the borohydride was in fact added, as all SM had reacted). The reaction mixture was stirred at RT for 1 h and then concentrated in vacuo to remove THF. The residue was partitioned between ethyl acetate and 5% sodium chloride solution. The aqueous phase was re-extracted with ethyl acetate and the combined extracts dried over MgSO$_4$ and concentrated in vacuo to a waxy solid. This was crystallised twice from hexane to give 96 g (60%) of a white solid. (98% pure by HPLC)

1,3-Dicaprin 2-arachidonate (CAC)

Arachidonic acid (AA96, 78.8 g, 0.26 mol) was dissolved in dichloromethane (DCM, 425 ml). The resulting solution was stirred at RT under nitrogen and oxalyl chloride (33.9 ml, 49.4 g, 0.39 mol, 1.5 eq) added dropwise at 15-20° C. over 15 mins. The mixture was stirred at RT overnight and then concentrated in vacuo to remove DCM and excess oxalyl chloride. The residual oily acid chloride (GLA-Cl) was then added dropwise over 30-40 min at 10-15° C. (ice/water cooling) to a stirred solution of 1,3-dicaprin (94.2 g, 0.24 mol), DCM (450 ml), pyridine (19.1 ml, 18.6 g, 0.24 mol) and 4-dimethylaminopyridine (1.72 1.50 g, 0.014 mol, 0.06 equiv) at 10-15° C. The reaction mixture was stirred at RT under nitrogen overnight. Pyridine hydrochloride was removed by filtration and washed with DCM. The combined washing and filtrate was washed with 1×150 ml portions of 5% NaCl, 5% NaHCO$_3$, 0.1N HCl, 5% NaCl. The solution was then dried over MgSO$_4$ and the solvent removed in vacuo to a brown oil (171 g).

The scale of the above three reactions was the largest on which each was carried out. The borohydride reduction produced, in addition to 1,3-dicaprin, a by-product in variable yield. The presence of this by-product greatly affected the yield of the isolated pure 1,3-dicaprin; the by-product could only be removed by two crystallisations of the crude product. Since the final product, CAC, is purified by column chromatography, it is imperative that the 1,3-dicaprin used for the final step is as pure as possible!

412 g of crude CAC was produced as a brown oil from the above reactions. This material was purified on a series of silica columns using hexane followed by 1-3% ether/hexane. The purification required 7 or 8 columns, using 3-4 kilos of silica, and 100 liters of solvent.

The resulting product, a clear very pale yellow oil, (295 grams) was 95.8% pure by HPLC (C18 4.6×100 mm, eluted with 85/15 ACN/THF at 1 ml/min. UV detection λ210 nm). GC indicated a ratio of 66.3/32.1 C/A (1.6% impurity carried through from the 5% impurity in A).

Summary 295 g of glycerol 1,3-didecanoate-2-arachidonate (1,3-dicaprin-2-AA, CAC) has been prepared from decanoyl chloride (98%) and Arachidonic acid (95%) by a three-step process (scheme given below). It is a very pale yellow oil and was stored under nitrogen in the freezer. The HPLC purity is 95.8%.

Synthesis Example 7

1,3-Dioleoin 2-gammalinolenoate (Glycerol 1,3-dioctadeca-9Z-enoate 2-octadecatri(6-Z,9-Z,12-Z) enoate or OGO)

This triglyceride is known: a carbon-14 labelled version has been prepared by normal chemical synthesis and the normal unlabelled form by biochemical synthesis using lipases. OGO is not a major component of borage oil but its isomer OOG is (9%). The two intermediates used in the synthesis of CGC are known. The last step is novel.

The use of, the synthesis of from 1,3-dioleoin, and the purification of CGC are all believed novel. In general triglycerides CXC are preferred over OXO on patent and cost of goods grounds.

OGO was here prepared by reaction of 1,3-Doleoin with GLA-chloride in dichloromethane-pyridine. 1,3-Diolein was prepared by sodium borohydride reduction of 1,3-dioleoylpropan-2-one, which was in turn prepared by reaction of oleoyl chloride with 1,3-dihydroxyacetone. The intermediate 1,3-dioleolin must be handled with care since it can undergo acyl migration on exposure to acids, bases and heat. Older methods[7,8] of making 1,3-dioleoin, via mono-tritylglycerols or glycidyl esters was deemed less attractive because of more steps and acyl migration problems. The final product, OGO, was purified by careful column chromatography on silica which removed by-products.

Small Scale 1,3-dioleoylpropan-2-one 155.1 g Oleic acid (155.1 g, 0.55 mol, 1.0 equiv, Croda 094 RV05192) was dissolved in dichloromethane (DCM, 500 ml). The solution was stirred at room temperature (RT) under nitrogen and 104.4 g (1.5 eq 71 mls) oxalyl chloride (104.4 g, 71.8 ml, 0.82 mol, 1.5 equiv) was added dropwise at 15-20° C. over about 20 mins. The reaction mixture was stirred overnight at RT. The excess oxalyl chloride and DCM were removed in vacuo and the residual oily acid chloride was added dropwise over 15-20 min to a stirred suspension of 1,3-dihydroxyacetone dimer (22.5 g, 0.24 mol of monomer), pyridine (40.4 ml), 4-dimethylaminopyridine (1.83 g) and dichloromethane (DCM, 500 ml) at room temperature under nitrogen. The temperature of the reaction mixture was kept below 20° C. by cooling in an ice/water bath. The reaction mixture was stirred at RT under nitrogen overnight. The pyridine hydrochloride formed was removed by filtration and washed with DCM. The combined filtrate and washings were then washed with 1×150 ml portions of 5% NaCl, 5% NaHCO$_3$, 0.1N HCl, 5% NaCl. The solution was then dried over MgSO$_4$ and concentrated in vacuo to an orange/brown semi-solid. This was triturated in methanol and stored in the —fridge overnight. The solid deposited (90% pure by HPLC) was then crystallised from diisopropyl ether (DIPE) and methanol to give 51.3 g of an off white solid which was 95% pure by HPLC. Further crystallisation from DIPE/methanol yielded 41 g (27%) of a 98% pure product.

1,3-Diolein

The above ketone (32.8 g, 0.053 mol) was dissolved in tetrahydrofuran (THF, 250 ml). Water (10 ml) was then added, the solution cooled to 5° C., and sodium borohydride added portionwise below 10° C. The reaction was followed by HPLC (C18, ACN/THF 90/10 at 2 mls/min, λ210 nm) and after all the starting ketone had reacted the addition of the borohydride was stopped (830 mg,0.022 mol added). The mixture was then concentrated in vacuo to remove THF. The residue was partitioned between ethyl acetate and water. The aqueous phase was re-extracted with ethyl acetate and the combined extracts dried over MgSO$_4$ and concentrated in vacuo to an oil (~33 g) which solidified on cooling. The product (68% pure by HPLC) was crystallised from 100 ml hexane at −20° C. (in the freezer) overnight This product (92% pure 21.1 g) was recrystallised from hexane (50 ml) to give 18.28 g (56% yield) of a product 97.5% pure by HPLC.

1, 3-Diolein 2-gammalinolenoate (O-G-O)

γ-Linolenic acid (GLA95, 41.2 g, 0.15 mol, 1.1 equiv) was dissolved in dichloromethane (DCM, 250 ml). The resulting solution was stirred at RT under nitrogen and oxalyl chloride (19.1 ml, 28.2 g, 0.22 mol, 1.65 equiv) added dropwise over 5 mins. The mixture was stirred at RT overnight and then concentrated in vacuo to remove DCM and excess oxalyl chloride. The residual oily acid chloride (GLA-Cl) was then added dropwise over 15 min (ice/water cooling) to a stirred solution of 1,3-diolein (83.5 g, 0.13 mol), DCM (250 ml), pyridine (10.9 ml, 10.6 g, 0.14 mol) and 4-dimethylaminopyridine (0.49 g, 0.004 mol, 0.15 equiv) at 10-15° C. The temperature was maintained by ice-water cooling. The reaction mixture was stirred at RT under nitrogen overnight. Pyridine hydrochloride was removed by filtration and washed with DCM. The combined washing and filtrate was washed with 1×80 ml portions of 5% NaCl, 5% NaHCO$_3$, 0.1N HCl, 5% NaCl. The solution was then dried over MgSO$_4$ and the solvent removed in vacuo. The residual brown oil was purified by column chromatography on silica. Elution with hexane and then with 5% ether/hexane gave 63.6 g (54%) of a colourless oil. Purity determined by HPLC.

Summary 64 g of glycerol 1,3-oleoate-2-gammalinolenoate (1,3-dioleate-2-GLA, OGO) was prepared from oleoyl chloride (98%) by a three-step process (scheme given below). It was an almost colourless oil (slight yellow tinge) and is being stored under nitrogen in the freezer. The HPLC purity was 89.4%.

$^{13}$C NMR Data for Structured Lipids

GGG $\delta_C$ (125.7 MHz, CDCl$_3$) 172.69 (1C, C-2 carbonyl), 173.09 (2C, C-1, C-3 carbonyls)
CGC $\delta_C$ (125.7 MHz, CDCl$_3$) 172.76 (1C, C-2 carbonyl), 173.17 (2C, C-1, C-3 carbonyls)
CAC $\delta_C$ (125.7 MHz, CDCl$_3$) 172.65 (1C, C-2 carbonyl), 173.28 (2C, C-1, C-3 carbonyls)
C(DHLA)C $\delta_C$ (125.7 MHz, CDCl$_3$) 172.83 (1C, C-2 carbonyl), 173.30 (2C, C-1, C-3 carbonyls)
GCG $\delta_C$ (125.7 MHz, CDCl$_3$) 172.91 (1C, C-2 carbonyl), 173.11 (2C, C-1, C-3 carbonyls)
OGO $\delta_C$ (125.7 MHz, CDCl$_3$) 172.69 (1C, C-2 carbonyl), 173.25 (2C, C-1, C-3 carbonyls)
AAA $\delta_C$ (125.7 MHz, CDCl$_3$) 172.66 (1C, C-2 carbonyl), 173.04 (2C, C-1, C-3 carbonyls)
CCC $\delta_C$ (125.7 MHz, CDCl$_3$) 172.81 (1C, C-2 carbonyl), 173.21 (2C, C-1, C-3 carbonyls)

Experimental Procedure

The proton-decoupled $^{13}$C NMR spectra with suppressed NOE were collected at 21° C. in a 5-mm broadband probe on a Joel 500 MHz spectrometer operating at 125.728 MHz. Waltz decoupling was the chosen mode of decoupling and was gated on only during the 14.89s acquisition time. The relaxation delay was set at 30 secs and the pulse angle was 90°. The spectral window used was ca.35 ppm (from 173.5 to 172.6 ppm) with a 170 ppm offset. The spectra were internally referenced to CDCl$_3$ at 77.0 ppm. Typically, the approximate number of scans collected for adequate signal-to-noise ranged from 300 to 1200 scans depending on the concentration and purity of the sample. The total acquisition time for the experiments ranged between 2-8 h e.g 1272 scans; data points 65,536. Concentrated solutions up to 20% w/v were employed when possible to reduce the acquisition time The chemical shifts quoted vary with the concentration of the solution.

Biological Studies.

Chronic Relapsing Experimental Autoimmune Encephalomyelitis (CREAE) Studies.

Induction and Clinical Assessment of EAE

CREAE was induced in C57B1/6 and SJL mice. Animals were injected subcutaneously with 100 μg of the neuroantigen peptide MOG 35-55 (amino acid sequence MEVGWYR-SPFSRVVHLYRNGK Genemed Synthesis, Inc) or 1 mg of mouse spinal cord homogenate (SCH), in phosphate buffered saline (PBS), emulsified by sonication for 10 min at room temperature, in incomplete Freund's adjuvant (DIFCO, Detroit, USA) supplemented with 480 μg of *mycobacteria tuberculosis* and 60 μg of *Mycobacteria butyricium* (DIFCO, Detroit, USA) on days 0 and 7 as described previously (Morris-Downes, M M., et al 2002). In addition to optimise the disease mice also received 200 ng (intraperitoneally) of *Bordetella pertussis* toxin dissolved in PBS administered 1 hr and 24 hrs after immunization with the MOG neuroantigen and for SCH days 0, 1, 7 and 8.

Animals were weighed from day 5 onwards and examined daily for clinical neurological signs by two experienced investigators and graded according to a previously validated grading scheme (Morris-Downes, M M. et al 2002 and others): 0=normal; 1=limp tail and feet; 2=impaired righting reflex; 3=partial hind limb paralysis; 4=complete hindlimb paralysis; 5=moribund; 6=death. Animals exhibiting clinical signs of a lesser severity grade than typically observed were scored as 0.5 less than the indicated grade.

Reference

Morris-Downes, M M., et al (2002). Pathological and regulatory effects of anti-myelin antibodies in experimental allergic encephalomyelitis in mice. *J. Neuroimmunol.* 125. 114-124.

The mean group EAE score was compared for each test group compared to a respective control group by non-parametric statistical analysis (Mann Whitney U Test).

All MOG-CREAE studies comprised a treatment control group (C-C-C or saline as selected from the above study). Each structured lipid was tested at 3 dose levels, all treatments being orally administered for 2 weeks from day 7 after inoculation. All treatment groups will contained 10 animals. On completion of studies (day 21), brain and spinal cord were be removed and half of the samples were processed for signs of CNS perivascular mononuclear leucocyte-infiltrated sites and demyelination.

Studies were as Follows:

Study 2: Spinal cord homogenate(SCH) EAE in SJL mice.
EAE Induction: 1 mg SCH day 0+day 7 sc. 200 ng Pertussis toxin day 0, 1, 7 & 8 ip.10mice/group. Mice were treated from day 7 to 21 with CCC or CGC.

Study 3: SCH EAE in SJL mice: Treatment was from PSD 7 to 21, both days inclusive.

Study 4: MOG EAE in C57BL mice: Treatment was from PSD 7 to 21, both days inclusive.

Study 5: SCH EAE in SJL mice: Treatment was from PSD 5 to 18, both days inclusive.

Study 6: MOG EAE in C57BL mice: Treatment was from Days 5 to 21 inclusive except C-DHLA-C group where treatment was from days 5 to 15 inclusive. Animals were culled on PSD 25. [Five animals from an untreated group, 3 animals from control CCC treatment group, 5 animals from GGG 150 ul treatment group and 2 animals from GGG 350 ul treatment group were sampled for histological analysis on PSD 20].

Study 7: SCH EAE in SJL Mice
Treatment was from Days 6 to 20 inclusive.

Study 2—Spinal cord homogenate (SCH) in SJL mice:—tested
CGC (50/150/350 ul); CCC (350 ul).
GGG. (50/350 ul)
[Severe disease observed]

Study 3—SCH/SJL mice:—tested
CCC (50/150/350 ul)
CGC (25150/150/350 ul)
GGG (50/150/350 ul)
OGO. (25/50/150/350 ul)
[Severe disease observed]

Study 4—MOG/C57BL mice:—Tested
CCC (50/150/350 ul)
CGC (25/50/150/350 ul)
GGG (50/150/350 ul)
OGO. (25/50/150/350 ul)

Study 6—MOG/C57BL mice:—Tested
CCC (150 ul)
C-DHLA-C (50 ul)
CAC (50/350 ul)
AAA (50/150 ul)
GCG (50 ul)
CGC (50 ul)
GGG. (150/350 ul)
[Pathology: CCC; GGG]

Histological examination of the submitted samples of brain and spinal cord showed lesions typical of experimental allergic encephalomyelitis.

Localised and diffuse lesions were characterised by gliosis, myelin vacuolation, axonal degeneration and perivascular cuffing with lymphocytes, macrophages and neutrophils.

Spinal cord lesions were mostly located in subpial white matter and brain lesions mostly occurred in the cerebellar white matter. Lesions were more severe in the spinal cords than in the brains and whereas all animals with brain lesions had lesions in the spinal cord, not all animals with cord lesions had lesions in the brain.

Variation in the severity of changes between individual mice is summarised using a semi-quantitative five point grading system.

Untreated mice had histological scores of 3-4 which correlated with EAE scores of 1.5-3. One mouse showed little pathological change with a zero score. In the GGG treated mice, the majority showed no abnormalities. Two mice from this group had histological scores of 2 and 3 respectively which correlated with EAE severity. scores of 1 and 1.5

The results of the four studies are shown in FIGS. 11 to 20 below

These show that the compounds G-G-G, A-A-A, C-G-C, C-DHGLA-C, and C-A-C are all capable of reducing severity of CREAE whereas compounds G-C-G and C-C-C failed to treat the condition. Compound O-G-O is believed to work if the dose is adjusted.

As cautioned in the description, the arachidnoic acid compounds are effective, but lead to death of some animals. Surviving animals had much reduced disease. It is believed that the dose of these compounds may be reduced still further to provide survival with satisfactory treatment.

Some of the studies show a bell shaped response curve for compounds C-G-C and G-G-G, suggesting that very high doses are not optimal, as set out above. Such dosing can be conveniently determined by those skilled art, eg. By dose escalatio and monitoring TGF-β1/TNF-α spontaneously release ratio changes from PBMCs.

Given the PCT/GB04/002089 high sn-2 γ-linolenic acid results, the lack of efficacy of low sn-2 black-current oil and G-C-G in CREAE and the low dose efficacy of C-G-C and C-DHGLA-C in FIG. 20, it can be seen that sn-2-γ-linolenic acid, dihomo-γ-linolenic acid and arachidonic acid lipids provide a novel treatment for MS that far exceeds any current therapy outcome in that lesions are repaired and difficult symptoms are resolved: decreasing EDSS over a period of years being so far unachieved in other treatments.

REFERENCES

Amor S, Groome N, Linington C, Morris M M, Dommair K, Gardinier M V, Matthieu J M, Baker D. Identification of epitopes of myelin oligodendrocyte glycoprotein for the induction of experimental allergic encephalomyelitis in SJL and Biozzi AB/H mice. J Immunol. 1994 Nov. 15; 153(10):4349-56.

Beck J, Rondot P, Catinot L et al. Increased production of interferon gamma and tumor necrosis factor precedes clinical manifestation in multiple sclerosis: do cytokines trigger off exacerbations? Acta Neurol Scand 1988; 78:318-23.

Bertolotto A, Capobianco M, Malucchi S et al. Transforming growth factor beta1 (TGFbeta1) mRNA level correlates with magnetic resonance imaging disease activity in multiple sclerosis patients. Neurosci Lett 1999; 263:21-4.

Bertolotto A, Malucchi S, Capobianco M et al. Quantitative PCR reveals increased levels of tumor necrosis factor-alpha mRNA in peripheral blood mononuclear cells of multiple sclerosis patients during relapses. J Interferon Cytokine Res 1999; 19:575-81.

Brosnan C F., Selmaj K and Raine C S. Hypothesis: a role for tumor necrosis factor in immune-mediated demyelination and its relevance to multiple sclerosis. *J Neuroimmunol* 1988:18, 87-94.

Brosnan C F and Raine C S. Mechanisms of immune injury in multiple sclerosis. *Brain Pathol.* 1996:6, 243-257.

Burns J, Bartholomew B, Lobo S. Isolation of myelin basic protein-specific T cells predominantly from the memory T-cell compartment in multiple sclerosis. Ann Neurol 1999; 45:33-9.

Cannella B, Raine C S. The adhesion molecule and cytokine profile of multiple sclerosis lesions. Ann Neurol 1995; 37:424-35.

Chou Y K, Bourdette D N, Offner H et al. Frequency of T cells specific for myelin basic protein and myelin proteolipid protein in blood and cerebrospinal fluid in multiple sclerosis. J Neuroimmunol 1992; 38:105-14.

De Stefano N., Narayanan S., Francis G S., Amaoutelis R., Tartaglia M C., Antel J P., matthews P M and Arnold D L. Evidence of axonal damage in the early stages of multiple sclerosis and its relevance to disability. *Arch Neurol.* 2001: 58(1), 65-70.

Ewing C, Bernard C C. Insights into the aetiology and pathogenesis of multiple sclerosis. Immunol Cell Biol 1998; 76:47-54.

Fazakerly J K Molecular biology of multiple sclerosis. Wiley and Sons Ltd. 1997, 255-273.

Fredrikson S, Soderstrom M, Hillert J et al. Multiple sclerosis: occurrence of myelin basic protein peptide-reactive T cells in healthy family members. Acta Neurol Scand 1994; 89:184-9.

Genain C P., Cannella B., hauser S L and Raine C S. Identification of autoantibodies associated with myelin damage in multiple sclerosis. *Nature Med* 1999:5, 170-175.

Gross C E, Bednar M M, Howard D B and Spom M B (1993) Transforming growth factor beta I reduces infarct size after experimental cerebral ischemia in a rabbit model. *Stroke* 24, 558-562.

Harbige, L S, Crawford MA, Jones J, Preece A W and Forti A. Dietary intervention studies on the phosphoglyceride fatty acids and electrophoreitic mobility of erythrocytes in multiple sclerosis. *Prog. Lipid Res* 1986:25, 243-248.

Harbige L S. Nutrition and immunity with emphasis on infection and autoimmune disease. (1996) *Nutr Health,* 10(4): 285-312.

Harbige L S (1998) Dietary n-6 and n-3 fatty acids in immunity and autoimmune disease. *Proceedings of the Nutrition Society* 57, 555-562.

Harbige L S, Yeatman N, Amor S & Crawford M A (1995) Prevention of experimental autoimmune encephalomyelitis in Lewis rats by a novel source of γ-linolenic acid. *British Journal of Nutrition* 74, 701-715.

Harbige L S., Layward L., Morris-Downes M M., Dumonde D C and Amor S. The protective effects of omega-6 fatty acids in experimental autoimmune encephalomyelitis (EAE) in relation to transforming growth factor-beta 1 (TGF-beta1) up-regulation and increased prostaglandin E2 (PGE2) production. *Clin Exp Immunol* 2000;122, 445-452.

Henrich Noack P, Prehn J H, and Kriegistein J. (1996) TGF-beta I protects hippocampal neurons against degeneration caused by transient global ischaemia. Dose-response relationship and potential neuroprotective mechanisms. *Stroke,* 27, 1609-1614.

Hirsch R L, Panitch H S, Johnson K P. Lymphocytes from multiple sclerosis patients produce elevated levels of gamma interferon in vitro. J Clin Immunol 1985; 5:386-9.

Hollifield R D, Harbige L S, PhM-Dinh D, Sharief M. Evidence for cytokine Dysregulation in Multiple Sclerosis: Peripheral Blood Mononuclear cell production of pro-inflammatory and anti-inflammatory cytokines during relapse and remission. *Autoimmunity,* 2003 36(3):133-141.

Imamura K, Suzumura A, Hayashi F et al. Cytokine production by peripheral blood monocytes/macrophages in multiple sclerosis patients. Acta Neurol Scand 1993; 87:281-5.

Issazadeh S, Lorentzen J C, Mustafa M I et al. Cytokines in relapsing experimental autoimmune encephalomyelitis in DA rats: persistent mRNA expression of proinflammatory cytokines and absent expression of interleukin-10 and transforming growth factor-beta. J Neuroimmunol 1996; 69:103-15.

Johns L D, Sriram S Experimental allergic encephalomyelitis: neutralizing antibody to TGF beta 1 enhances the clinical severity of the disease. J Neuroimmunol 1993; 47:1-7.

Kerlero de Rosbo N, Hoffman M, Mendel I et al. Predominance of the autoimmune response to myelin oligodendrocyte glycoprotein (MOG) in multiple sclerosis: reactivity to the extracellular domain of MOG is directed against three main regions. Eur J Immunol 1997; 27:3059-69.

Kerlero de Rosbo N, Milo R, Lees M B et al. Reactivity to myelin antigens in multiple sclerosis. Peripheral blood lymphocytes respond predominantly to myelin oligodendrocyte glycoprotein. J Clin Invest 1993; 92:2602-8.

Khalil N. TGF-beta: from latent to active. Microbes Infect 1999; 1: 1255-63.

Krupinski J, Kumar P, Kumar S, and Kaluza J. (1996) Increased expression of TGF-beta I in brain tissue after ischemic stroke in humans. *Stroke,* 27, 852-857.

Kuroda Y, Shimamoto Y. Human tumor necrosis factor-alpha augments experimental allergic encephalomyelitis in rats. J Neuroimmunol 1991; 34:159-64.

Lu C Z, Jensen M A, Arnason B G. Interferon gamma- and interleukin-4-secreting cells in multiple sclerosis. J Neuroimmunol 1993; 46:123-8.

Maimone D, Reder A T, Gregory S. T cell lymphokine-induced secretion of cytokines by monocytes from patients with multiple sclerosis. Cell Immunol 1993; 146:96-106.

Martino G, Hartung H-P. Immunopathogenesis of multiple sclerosis: the role of T cells. Curr Opin Neurol 1999; 12:309-21.

McCarron R M, Wang L, Racke M K et al. Cytokine-regulated adhesion between encephalitogenic T lymphocytes and cerebrovascular endothelial cells. J Neuroimmunol 1993; 43:23-30.

McDonald W I, Compston A, Edan G, Goodkin D, Hartung H P, Lublin F D, McFarland H F, Paty D W, Polman C H, Reingold S C, Sandberg-Wollheim M, Sibley W, Thompson A, van den Noort S, Weinshenker B Y, Wolinsky J S. Recommended diagnostic criteria for multiple sclerosis: guidelines from the International Panel on the diagnosis of multiple sclerosis. Ann Neurol. 2001 July; 50(1):121-7.

Merrill J E, Strom S R, Ellison G W et al. In vitro study of mediators of inflammation in multiple sclerosis. J Clin Immunol 1989; 9:84-96.

Merrill J E, Zimmerman R P. Natural and induced cytotoxicity of oligodendrocytes by microglia is inhibitable by TGF beta. Glia 1991; 4:327-31.

Miyazono K, Hellman U, Wernstedt C et al. Latent high molecular weight complex of transforming growth factor beta 1. Purification from human platelets and structural characterization. J Biol Chem 1988; 263:6407-15.

Mokhtarian F, Shi Y, Shirazian D et al. Defective production of anti-inflammatory cytokine, TGF-beta by T cell lines of patients with active multiple sclerosis. J Immunol 1994; 152:6003-10.

Navikas V, Link H. Review: cytokines and the pathogenesis of multiple sclerosis. J Neurosci Res 1996; 45:322-33.

Noseworthy J H. Progress in determining the causes and treatment of multiple sclerosis. Nature 1999:399(6738 Suppl), A40-47.

Ota K, Matsui M, Milford E L et al. T-cell recognition of an immunodominant myelin basic protein epitope in multiple sclerosis. Nature 1990; 346:183-7.

Perkin G D, Wolinsky J S. Fast facts-Multiple Sclerosis, 1st Edn. Oxford, UK: Health Press, 2000.

Philippe J, Debruyne J, Leroux-Roels G et al. In vitro TNF-alpha, IL-2 and IFN-gamma production as markers of relapses in multiple sclerosis. Clin Neurol Neurosurg 1996; 98:286-90.

Phylactos A C, Ghebremeskel K, Costeloe K, Leaf A A, Harbige L S, Crawford M A. (1994) Polyunsaturated fatty acids and antioxidants in early development. Possible prevention of oxygen-induced disorders. Eur J Clin Nutr. 48Suppl 2:S17-23.

Prehn J H, Peruche B, Unsicker K and Kriegistein J. (1993) Isoform-specific effects of transforming growth factor-beta on degeneration of primary neuronal cultures induced by cytotoxic hypoxia or glutamate. *J.Neurochem.* 60, 1665-1672.

Rack M K, Sriram S, Calrimi J, Cannella B, Raine C S & McFarim D E (1993) Long-term treatment of chronic relapsing experimental allergic encephalomyelitis by transforming growth factor-p2. *Journal of Neuroimmunology,* 46, 175-183.

Racke M K, Cannella B, Albert P et al. Evidence of endogenous regulatory function of transforming growth factor-beta 1 in experimental allergic encephalomyelitis. Int Immunol 1992; 4:615-20.

Rieckmann P, Albrecht M, Kitze B et al. Cytokine mRNA levels in mononuclear blood cells from patients with multiple sclerosis. Neurology 1994; 44:1523-6.

Rieckmann P, Albrecht M, Kitze B et al. Tumor necrosis factor-alpha messenger RNA expression in patients with relapsing-remitting multiple sclerosis is associated with disease activity. Ann Neurol 1995; 37:82-8.

Ruddle N H, Bergman C M, McGrath K M et al. An antibody to lymphotoxin and tumor necrosis factor prevents transfer of experimental allergic encephalomyelitis. J Exp Med 1990; 172:1193-200.

Santambrogio L, Hochwald G M, Saxena B, Leu C H, Martz J E, Carlino J A, Ruddle N H, Palladino M A, Gold L I & Thorbecke G J (1993) Studies on the mechanisms by which Transforming Growth Factor-p protects against allergic encephalomyelitis. *Journal of Immunology* 151, 1116-1127.

Schiefer H B, Hancock D S, Loew F M. Long-term effects of partially hydrogenated herring oil on the rat myocardium. Drug Nutr Interact. 1982; 1(2):89-102.

Schluesener H J, Lider O. Transforming growth factors beta 1 and beta 2: cytokines with identical immunosuppressive effects and a potential role in the regulation of autoimmune T cell function. J Neuroimmunol 1989; 24:249-58.

Selmaj K, Raine C S, Cannella B et al. Identification of lymphotoxin and tumor necrosis factor in multiple sclerosis lesions. J Clin Invest 1991; 87:949-54.

Selmaj K, Raine C S, Farooq M et al. Cytokine cytotoxicity against oligodendrocytes. Apoptosis induced by lymphotoxin. J Immunol 1991; 147:1522-9.

Sharief M K, Thompson E J. In vivo relationship of tumor necrosis factor-alpha to blood-brain barrier damage in patients with active multiple sclerosis. J Neuroimmunol 1992; 38:27-33.

Tejada-Simon M V, Hong J, Rivera V M et al. Reactivity pattern and cytokine profile of T cells primed by myelin peptides in multiple sclerosis and healthy individuals. Eur J Immunol 2001; 31:907-17.

Vartanian T, Li Y, Zhao M et al. Interferon-gamma-induced oligodendrocyte cell death: implications for the pathogenesis of multiple sclerosis. Mol Med 1995; 1:732-43.

Vivien D, Bemaudin M, Buisson A, Divoux D, MacKenzie E T and Nouvelot A.(1998) Evidence of type I and type II transforming growth factor-beta receptors in central nervous tissues: changes induced by focal cerebral ischemia. J. Neurochem. 70, 2296-2304.

Zhang J, Markovic-Plese S, Lacet B et al. Increased frequency of interleukin 2-responsive T cells specific for myelin basic protein and proteolipid protein in peripheral blood and cerebrospinal fluid of patients with multiple sclerosis. J Exp Med 1994; 179:973-84.

Japanese Patent 6172263 (1994) Y. Kosugi et al, Agency of Industrial Science & Technology High-purity arachidonic acid triglyceride and its production.

U.S. Pat. No. 4,888,324 (1989) N. Catsimpoolas et al, Angio-Medical Corporation Method for enhancing angiogenesis with lipid containing molecules.

Y. Kosugi and N. Azuma, J. Amer. Oil Chem. Soc., 71, 1397-1403 (1994). Synthesis of Triacylglycerol from polyunsaturated fatty acid by immobilized ipase.

J. W. Hageman et al, J. Amer, Oil Chem. Soc., 49, 118-xxx (1972) Preparation of Glycerin and their Uses.

E. S. Lutton and A. J. Fehl, Lipids, 5, 90-99 (1970). The polymorphism of odd and even saturated single acid triglycerides, C8-C22.

D. Horrobin, A. McMordie, M. S. Manku (Scotia Holdings PLC UK) Eur. Pat. Appl EP 609078 3 Aug. 1994. Phospholipids containing two different unsaturated fatty acids for use in therapy, nutrition, and cosmetics.

Y.-S. Huang, X. Lin, P. R. Redden and D. F. Horrobin, J. Am. Oil Chem. Soc., 72, 625-631, (1995). In vitro Hydrolysis of Natural and Synthetic γ-Linolenic Acid-Containing Triacylglycerols by Pancreatic Lipase K. Osada, K. Takahashi, M. Hatano and M. Hosokawa, Nippon Suisan Gakkaishi., 57, 119-125 (1991). Chem. Abstr., 115:278299 Molecular Species of Enzymically-synthesized Polyunsaturated Fatty acid-rich Triglycerides.

J.-W. Liu, S. DeMichele, M. Bergana, E. Bobik, Jr., C. Hastilow, Lu-Te Chuang, P. Mukerji and J.-S. Huang., J. Am. Oil Chem. Soc., 78, 489-493 (2001) Characterization of Oil Exhibiting High γ-Linolenic Acid from a Genetically transformed Canola Strain.

D. R. Kodali, D. Atkinson, T. G. Redgrave and D. Small, J Lipid Res., 28, 403-413 (1987). Structure and polymorphism of 18-Carbon Fatty Acid Triacylglycerols: Effect of Unsaturation and Substitution in the 2-Position P. H. Bentley and W. McCrae, J. Org. Chem. 35, 2082-2083 (1970) An Efficient Synthesis of Symmetrical 1,3-Diglycerides.

M. Berger, K. Laumen and M. P. Schneider, J. Am. Oil. Chem. Soc., 69, 955-959, (1992). Enzymatic Esterification of Glycerol 1. Lipase-Catalyzed Synthesis of Regioisomerically Pure 1,3-sn-Diacylglycerols.

A. P. J. Mank, J. P. Ward and D. A. van Dorp, Chem. Physics Lipids, 16, 107-114 (1976). A versatile, flexible synthesis of 1,3-diglycerides and triglycerides.

L. Hartman, Chem. Rev., 58, 845-867 (1958) and references therein. Advances in the Synthesis of Glycerides of Fatty Acids

TABLE 1

Compositional (% Total FAs) Characteristics of Various Oils and their Protective Effects in EAE

| Treatment | 18:2n-6 | 18:3n-6 | 18:2n-6/18:3n-6 | 18:1n-9 | INCIDENCE OF EAE |
|---|---|---|---|---|---|
| FGO | 17 | 20 | 0.6 | 35 | 0/10 |
| BOO | 37 | 24 | 1.5 | 15 | 3/10 |
| EPO | 71 | 9.4 | 7.5 | 9 | 7/10 |
| SAF | 66 | — | — | 17 | 9/10 |
| Controls | — | — | — | — | 9/10 |

FGO, Fungal Oil;
BOO, Borage Oil;
EPO, Evening Primrose Oil,
SAF, Safflower Oil.

TABLE 2

Treatment Groups-PCT/GB04/002089 Borage oil-MS trial

| | | Female | Male | Mean Relapse Rate (in past two years) | Mean Base EDSS | Number |
|---|---|---|---|---|---|---|
| Group | Placebo | 7 | 4 | 2.6 | 3.9 | 11 |
| | Low Dose | 5 | 2 | 2.9 | 3.5 | 7 |
| | High Dose | 8 | 2 | 3.4 | 2.8 | 10 |
| Total | | 20 | 8 | 2.9 | 3.4 | 28 |

TABLE 3

Molecular Species Comparison of Triacylglycerol-GLA (TG-GLA), Ethyl-Ester-GLA (EE-GLA) and PCT/GB04/002089 Borago Officinalis Oil-GLA (BOR-GLA) in MOG-induced CREAE in SJL Mice

| Treatment | No. with EAE | Mean Clinical Score |
|---|---|---|
| Control | 10/11 | 3.3 ± 1.3 |
| EE-GLA[a] | 5/6 | 3.0 ± 0.8 |
| TG-GLA[a] | 3/6 | 1.0 ± 1.3[c] |
| BOR-GLA[b] | 3/6 | 1.0 ± 1.2[c] |

[a]Animals given 100 µl of test lipid;
[b]250 µl BOR-GLA given. Significance of difference compared with controls,
[c]p < 0.05

TABLE 4

Effect of enriched black-currant seed oil (73% GLA) on the incidence of EAE

| | % Incidence of EAE (Days after immunisation) | | |
|---|---|---|---|
| | 13 | 17 | 21 |
| Controls (n = 10) | 60 | 90 | 10 |
| Blackcurrant (n = 10) | 10 | 80 | 70 |

Note:

Blackcurrant oil delays the incidence but does not provide full protection. Animals were fed 7 days after sensitization (immunisation).

The invention claimed is:

1. A method of treating a patient in need of therapy for multiple sclerosis comprising administering to that patient a therapeutically effective dose of a lipid glyceride selected from the group consisting of:
    glycerol 1,3-didecanoate-2-octadeca (6-Z, 9-Z, 12-Z) trienoate and
    glycerol 1,3-didecanoate-2-eicosa (8-Z, 11-Z, 14-Z) trienoate.

2. A method as claimed in claim 1 wherein multiple sclerosis is relapsing remitting multiple sclerosis, primary progressive multiple sclerosis or chronic progressive multiple sclerosis.

3. A method as claimed in claim 1 wherein the amount of the lipid glyceride administered is between 0.5 and 30 grams per day.

4. A method as claimed in claim 3 wherein the amount of the lipid glyceride administered is 3 to 5 grams per day.

* * * * *